US008263800B2

(12) United States Patent
Murphy et al.

(10) Patent No.: US 8,263,800 B2
(45) Date of Patent: Sep. 11, 2012

(54) PARTIALLY FLUORINATED SULFONATED SURFACTANTS

(75) Inventors: Peter Michael Murphy, Chadds Ford, PA (US); Tracy Hewat, Edinburgh (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1106 days.

(21) Appl. No.: 12/165,798

(22) Filed: Jul. 1, 2008

(65) Prior Publication Data

US 2010/0003737 A1 Jan. 7, 2010

(51) Int. Cl.
*C07C 69/34* (2006.01)
*C11D 3/50* (2006.01)
*C11D 1/12* (2006.01)

(52) U.S. Cl. ......... 560/197; 560/190; 510/101; 510/489

(58) Field of Classification Search ........................ None
See application file for complete search history.

(56) References Cited

U.S. PATENT DOCUMENTS

| | | |
|---|---|---|
| 2,951,770 A | 9/1960 | Lodge et al. |
| 3,133,886 A | 5/1964 | Zisman et al. |
| 3,686,281 A | 8/1972 | Knell et al. |
| 3,979,469 A | 9/1976 | Jäger |
| 4,018,689 A | 4/1977 | Thompson |
| 4,167,639 A | 9/1979 | Billenstein et al. |
| 4,473,371 A | 9/1984 | Schinzel et al. |
| 4,545,939 A | 10/1985 | Sekiguchi et al. |
| 5,202,506 A | 4/1993 | Kirchner et al. |
| 5,481,028 A | 1/1996 | Petrov et al. |
| 5,643,864 A | 7/1997 | Li et al. |
| 5,865,851 A | 2/1999 | Sidoti et al. |
| 6,048,941 A | 4/2000 | Yamana et al. |
| 6,054,615 A | 4/2000 | Qiu |
| 6,376,705 B1 | 4/2002 | Qiu |
| 6,472,054 B1 | 10/2002 | Aurenty et al. |
| 2003/0148232 A1 | 8/2003 | Orem et al. |
| 2004/0137385 A1 | 7/2004 | Orem et al. |
| 2005/0107645 A1 | 5/2005 | Furukawa |
| 2006/0148671 A1 | 7/2006 | Dams et al. |
| 2007/0004938 A1 | 1/2007 | Guerra |
| 2007/0104669 A1 | 5/2007 | Muller |
| 2007/0128147 A1 | 6/2007 | Schwartz et al. |
| 2007/0160555 A1 | 7/2007 | Staudigel et al. |
| 2007/0218371 A1 | 9/2007 | Elliott et al. |
| 2008/0093582 A1 | 4/2008 | Nagai et al. |

FOREIGN PATENT DOCUMENTS

| | | |
|---|---|---|
| CA | 1335388 | 4/1994 |
| GB | 1467988 A | 3/1977 |
| GB | 2 302 879 A | 2/1997 |
| JP | 62209200 | 9/1987 |
| JP | 63048202 | 2/1988 |
| JP | 01271484 | 10/1989 |
| JP | 06328849 | 11/1994 |
| JP | 08337976 A | 12/1996 |
| JP | 10245370 A | 9/1998 |
| JP | 2000158815 A | 6/2000 |
| JP | 2006056982 A | 3/2006 |
| SU | 523086 | 1/1977 |
| SU | 1728236 | 4/1992 |
| WO | WO 95/11877 | 5/1995 |
| WO | WO 97/00990 | 1/1997 |
| WO | WO 97/46283 | 12/1997 |
| WO | WO 2007060300 | 5/2007 |

OTHER PUBLICATIONS

Pittman et al., Reactions and Wetting Properties of 1:1 Perfluoroalkyl Allyl and Methallyl Ether-Maleic Anjydride Copolymers; Journal of Polymer Science Polymer Chemistry Edition (1974), 12(3), 521-534; Publisher: John Wiley & Sons, Inc.
Gol'Din et al., Surface activity of fluoroorganic esters of sulfosuccinic acid; Kolloidnyi Zhurnal (1977), 39(1), 134-136, Russia. Abstract.
Gol'Din et al., Synthesis of alkali metal salts of fluoroorganic esters of sulfosuccinic acid; Zhurnal Obshchei Knimii (1977), 47(5), 1086-1088, Russia. Abstract.
Greiner et al., Fluorosurfactants based on alcohol telomers; Abhandlungen der Akademie der Wissenschaften der DDR (1977), Volume Date 1976, 1 (Originalbeitr.—Int. Tag. Grenzflaechenakt. Stoffe, 4$^{th}$, Teil 1), 179-185; Germany. Abstract.
Yoshino et al., Syntheses of anionic surfactants having two polyfluoroalkyl chains and their flocculation ability for dispersed magnetite particles in water; Bulletin of the Chemical Society of Japan (1991), 64(11), 3262-3266, Japan. Abstract.
Gol'Din et al., Synthesis and activity of dialkyl- and bis(fluoroalkyl) sulfosuccinates; Zhurnal Prikladnoi Khimii (Sankt-Peterburg, Russian Federation) (1992), 65(9), 2038-2044; Russia. Abstract.
Balague et al., Synthesis of fluorinated telomers. Part 1. Telomerization of vinylidene fluoride with perfluoroalkyl iodides; Journal of Fluorine Chemistry (1995), 70, 215-223.; Publisher: Elsevier Science S.A.

(Continued)

*Primary Examiner* — Jehanne Sitton

(57) ABSTRACT

The present invention comprises a compound comprising Formula 1A, 1B, or 1C $(R_a-O-CO-)_2X$  Formula 1A $R_a-O-CO-X-CO-O-(CH_2CH_2)R_f$  Formula 1B $R_a-O-CO-X-CO-O-R$  Formula 1C wherein
$R_a$ is the group $R_f(CH_2CF_2)_d-(C_gH_{2g})-$; $R_fOCF_2CF_2-(C_gH_{2g})-$; $R_fOCFHCF_2O(CH_2CH_2O)_v-(C_gH_{2g})-$; $R_fOCFHCF_2O(C_wH_{2w})$; $R_fOCF(CF_3)CONH-(C_gH_{2g})$; or $R_f(CH_2)_h[(CF_2CF_2)_i(CH_2CH_2)_j]_k$;
$R_f$ is $C_cF_{(2c+1)}$;
d is 1 to about 3; g is 1 to 4; v is 1 to about 4; w is from about 3 to about 12; h is 1 to about 6; i, j, and k are each independently 1, 2, or 3, or a mixture thereof; provided that the total number of carbon atoms in group (vi) is from about 8 to about 22;
X is a linear or branched difunctional alkyl sulfonate group $-C_eH_{(2e-1)}(SO_3M)-$, wherein e is 2 or 3;
M is a monovalent cation selected from the group consisting of hydrogen, ammonium, alkali metal, or alkaline earth metal;
R is H or a linear or branched alkyl group $C_bH_{(2b+1)}-$; and b is from 1 to about 18.

11 Claims, No Drawings

OTHER PUBLICATIONS

Yoshino et al., Surfactants having polyfluoroalkyl chains. II. Syntheses of anionic surfactants having two polyfluoroalkyl chains including a trifluoromethyl group at each tail and their flocculation-redispersion ability for dispersed magnetite particles in water; Journal of Fluorine chemistry (1995), 70(2), 187-191; Publisher: Elsevier Science S.A.

Roberts, Sulfonation Technology for Anionic Surfactant Manufacture; Organic Process Research & Development (1998), 2, 194-202.

Szonyi et al., Synthesis of new amphoteric perfluoroalkylated double-chain and triple-chain amphiphiles; Rivista Italiana delle Sostanze Grasse (1998), 75(2), 83-91; Publisher: Stanzione Sperimentale per le Industrie degli Oli e dei Grassi. Abstract.

Abe et al., Shapes and sizes of sulfosuccinate-type fluorocarbon surfactant vesicles in aqueous solutions; Shikizai Kyokaishi (2000), 73(2), 53-59; Publisher: Shikizai Kyokai, Japan. Abstract.

Liu et al., Water in Carbon Dioxide Microemulsions with Fluorinated Analogues of AOT; Langmuir (2001), 17(2), 274-277.

Yoshino, Double Chain-Type Fluorinated Surfactants; Review: J. Jpn. Soc. Colour Mater. (Shikizai), 74(4), 196-204 (2001).

Eastoe et al., Effects of Fluorocarbon Surfactant Chain Structure on Stability of Water-in-Carbon Dioxide Microemulsions. Links between Aqueous Surface Tension and Microemulsion Stability; Langmuir (2002), 18, 3014-3017.

Brace et al., "Single tail" and "twin tail" 3-(perfluoroalkylethanethia)alkylsuccinic anhydrides give $R_F$ segmented diacids, amic acids, imides, esters, and salts. Unusual $^1H$ NMR of the succinamic acids; Journal of Fluorine Chemistry (2003) 121(1), 33-50; Publisher: Elsevier Science B.V.

Eastoe et al., Dynamic Surface Excesses of Fluorocarbon Surfactants; Langmuir (2003), 19(19), 7734-7739; Web Publisher: American Chemical Society.

Sagisaka et al., Interfacial Properties of Branch-Tailed Fluorinated Surfactants Yielding a Water/Supercritial $CO_2$ Microemulsion; Langmuir (2004), 20(7), 2560-2566. Web Publisher: American Chemical Society.

Acharya et al., Spectrofluorimetric study of esculin in micellar media; Journal of Indian Council of Chemists (2006), 23(2), 88-91; Publisher: Indian Council of Chemists. Abstract.

Liu et al., Microemulsions formed with novel fluorinated surfactants in supercritical carbon dioxide; Abstracts of Papers, $231^{st}$ ACS National Meeting, Atlanta, Georgia, USA, Mar. 26-30, 2006, COLL-020; Publisher: American Chemical Society, Washington, DC, USA. Abstract.

Sagisaka et al., Optimum Tail Length of Fluorinated Double-Tail Anionic Surfactant for Water/Supercritical $CO_2$ Microemulsion Formation; Langmuir (2007), 23(17), 8784-8788.

PARTIALLY FLUORINATED SULFONATED SURFACTANTS

BACKGROUND OF THE INVENTION

Historically, many fluoroalkyl surfactants were based on the perfluoroalkylethanols, $F(CF_2CF_2)_qCH_2CH_2OH$, the so-called "Telomer B alcohols", where q was typically about 2 to 10. The Telomer B alcohols and their preparation are described by Kirchner et al. in U.S. Pat. No. 5,202,506. Other fluoroalkyl surfactants based on Telomer B alcohols have included "twin-tailed" anionic surfactants such as $F(CF_2CF_2)_q(CH_2CH_2)OCOCH_2CH(SO_3Na)COO(CH_2CH_2)(CF_2CF_2)_qF$, where q is as defined above, prepared by firstly reacting two moles of one or more perfluoroalkylethanols with one of maleic anhydride and, secondly, reacting the diester product with sodium hydrogen sulfite solution, as described, for instance, by Yoshino et al. in "Surfactants having polyfluoroalkyl chains. II. Syntheses of anionic surfactants having two polyfluoroalkyl chains including a trifluoromethyl group at each tail and their flocculation-redispersion ability for dispersed magnetite particles in water", Journal of Fluorine Chemistry (1995), 70(2), 187-91. Yoshino et al. reported examples wherein q was 2, 3, and 4 for use in supercritical carbon dioxide. Yoshino et al. report twin-tailed surfactants wherein both end groups are limited to perfluoroalkyl groups.

Nagai et al. in US Patent Application 2008/0093582, describe twin-tailed surfactants of the structure

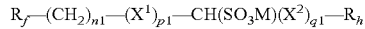

$$R_f-(CH_2)_{n1}-(X^1)_{p1}-CH(SO_3M)(X^2)_{q1}-R_h$$

wherein $R_f$ is a fluoroalkyl group that may contain an ether bond, $X^1$ and $X^2$ are the same or different divalent linking groups; M is H, an alkali metal, half an alkaline earth metal, or ammonium; $R_h$ is an alkyl group; n1 is an integer of 1 to 10; and p1 and q1 are each 0 or 1.

One common route to perfluoroalkylethanols used to make such surfactants is a multi-step process using tetrafluoroethylene. Tetrafluoroethylene is a hazardous and expensive intermediate with limited availability. It is desirable to provide fluorinated surfactants that use less or no tetrafluoroethylene in their preparation.

It is also desirable to provide new and improved fluorinated surfactants in which the perfluoroalkyl group of the prior art is replaced by partially fluorinated terminal groups that require less tetrafluoroethylene and show increased fluorine efficiency. By "fluorine efficiency" is meant the ability to use a minimum amount of fluorochemical to obtain a desired surface effect or surfactant properties, when applied to substrates, or to obtain better performance using the same level of fluorine. A polymer having high fluorine efficiency generates the same or greater level of surface effect using a lower amount of fluorine than a comparative polymer. The present invention provides such improved fluorinated surfactants.

SUMMARY OF THE INVENTION

The present invention comprises a compound comprising Formula 1A, 1B, or 1C

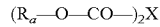

$(R_a-O-CO-)_2X$  Formula 1A

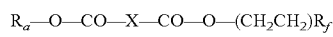

$R_a-O-CO-X-CO-O-(CH_2CH_2)R_f$  Formula 1B

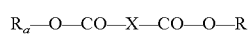

$R_a-O-CO-X-CO-O-R$  Formula 1C wherein
$R_a$ is the group
(i) $R_f(CH_2CF_2)_d-(C_gH_{2g})-$;
(ii) $R_fOCF_2CF_2-(C_gH_{2g})-$;
(iii) $R_fOCFHCF_2O(CH_2CH_2O)_v-(C_gH_{2g})-$;
(iv) $R_fOCFHCF_2O(C_wH_{2w})-$;
(v) $R_fOCF(CF_3)CONH-(C_gH_{2g})-$; or
(vi) $R_f(CH_2)_h[(CF_2CF_2)_i(CH_2CH_2)_j]_k-$
 each $R_f$ is independently $C_cF_{(2c+1)}$;
 c is 2 to about 6;
 d is 1 to about 3;
 g is 1 to about 4;
 v is 1 to about 4;
 w is from about 3 to about 12;
 h is 1 to about 6;
 i, j, and k are each independently 1, 2, or 3, or a mixture thereof; provided that the total number of carbon atoms in group (vi) is from about 8 to about 22;
X is a linear or branched difunctional alkyl sulfonate group

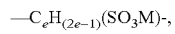

$-C_eH_{(2e-1)}(SO_3M)-$, wherein
 e is 2 or 3.
M is a monovalent cation selected from the group consisting of hydrogen, ammonium, alkali metal, and alkaline earth metal;
 R is H or a linear or branched alkyl group $C_bH_{(2b+1)}-$; and
 b is from 1 to about 18.

The present invention further comprises a method of altering the surface behavior of a liquid comprising adding to the liquid a compound of Formula 1A, 1B or 1C as described above, or a mixture thereof.

DETAILED DESCRIPTION

Herein trademarks are shown in upper case.

The surfactants of the present invention have the structure of Formulae 1A, 1B, or 1C.

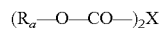
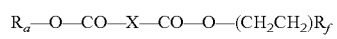
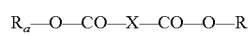

$(R_a-O-CO-)_2X$  Formula 1A $R_a-O-CO-X-CO-O-(CH_2CH_2)R_f$  Formula 1B $R_a-O-CO-X-CO-O-R$  Formula 1C wherein
 R is H or a linear or branched alkyl group $C_bH_{(2b+1)}-$ wherein b is from 1 to about 18, preferably from about 6 to about 18;
 each $R_f$ is independently $C_cF_{(2c+1)}$ having c of from about 2 to about 6, preferably from 2 to 4, and more preferably 4;
 X is a linear or branched difunctional alkyl sulfonate group

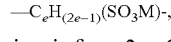

$-C_eH_{(2e-1)}(SO_3M)-$, wherein e is from 2 or 3, preferably 3; and M is a monovalent cation which is hydrogen, ammonium, alkali metal, or alkaline earth metal, and is preferably Na;
 $R_a$ is selected from the group consisting of structure (i) through (vi) wherein $R_f$ is as defined above, and g is 1 to about 4, preferably from 1 to 3, and more preferably 2:
 (i) $R_f(CH_2CF_2)_d-(C_gH_{2g})-$ wherein d is 1 to about 3, preferably from 1 to 2, and more preferably 1;
 (ii) $R_fOCF_2CF_2-(C_gH_{2g})-$;
 (iii) $R_fOCFHCF_2O(CH_2CH_2O)_v-(C_gH_{2g})-$ wherein v is 1 to about 4, preferably from 1 to 2, and more preferably 2;
 (iv) $R_fOCFHCF_2O(C_wH_{2w})-$ wherein w is from about 3 to about 12, preferably from 4 to 6, and more preferably 4;

(v) $R_fOCF(CF_3)CONH—(C_gH_{2g})—$; or
(vi) $R_f(CH_2)_h[(CF_2CF_2)_i(CH_2CH_2)_j]_k$ wherein h is 1 to about 6, preferably from 1 to 3, and more preferably 1; and i, j, and k are each independently 1, 2, or 3, or a mixture thereof, preferably 1 or 2, and more preferably 1; provided that the total number of carbon atoms in group (vi) is from about 8 to about 22. The preferred $R_a$ groups are (i), (ii), (iii), and (iv).

Preferred embodiments of Formula 1A, 1B and 1C are those wherein Ra is group (i) $R_f(CH_2CF_2)_d—(C_gH_{2g})—$, (ii) $R_fOCF_2CF_2—(C_gH_{2g})—$; (iii) $R_fOCFHCF_2O(CH_2CH_2)_v—(C_gH_{2g})—$; or (iv) $R_fOCFHCF_2O(C_wH_{2w})—$; when c is 3 or 4; and X is $CH_2CH(SO_3M)$, $CH_2CH(CH_2SO_3M)$, $CH(CH_3)CH(SO_3M)$, $CH_2CH(SO_3M)CH_2$, or $CH_2CH(SO_3M)CH_2CH_2$. More specifically preferred embodiments of Formula 1A, 1B and 1C are when d is 1, g is 1 or 2, and $R_f$ is $C_3F_7$ or $C_4F_9$. Also specifically preferred are compounds wherein $R_f$ is $C_3F_7$ or $C_4F_9$ and X is $C_3H_5(SO_3Na)$ or $CH_2CH(SO_3Na)$. The compound of Formula 1B wherein $R_a$ is $C_4F_9CH_2CF_2CH_2CH_2$ or $C_3F_7CH_2CF_2CH_2CH_2$ and $R_f$ is $(CF_2)_6F$ is also preferred.

A preferred embodiment of Formula 1A ($R_aOCO—X—COOR_a$) is $C_4F_9CH_2CF_2CH_2CH_2OC(O)C_3H_5(SO_3Na)C(O)OCH_2CH_2CF_2CH_2C_4F_9$.

A preferred embodiment of Formula 1B is $C_4F_9CH_2CF_2CH_2CH_2OC(O)CH_2CH(SO_3Na)C(O)OCH_2CH_2(CF_2)_6F$.

A preferred embodiment of Formula 1C is $C_4F_9CH_2CF_2CH_2CH_2OC(O)CH_2CH(SO_3Na)C(O)O(CH_2)_6H$.

The surfactants of Formulae 1A, 1B, and 1C economize on the use of tetrafluoroethylene in their preparation and provide comparable or improved surfactant properties, versus prior art surfactants derived from Telomer B alcohols.

The surfactants of Formulae 1A, 1B, and 1C are prepared via the unsaturated intermediates of Formulae 2A, 2B, and 2C according to the following Reaction Scheme A:

The unsaturated intermediates used in the preparation of Formula 1A, 1B and 1C are compounds of Formula 2A, 2B and 2C:

$(R_a—O—CO—)_2Y$  Formula 2A $R_a—O—CO—Y—CO—O—(CH_2CH_2)R_f$  Formula 2B $R_a—O—CO—Y—CO—O—R$  Formula 2C wherein
$R_a$ is the group
(i) $R_f(CH_2CF_2)_d—(C_gH_{2g})—$;
(ii) $R_fOCF_2CF_2—(C_gH_{2g})—$;
(iii) $R_fOCFHCF_2O(CH_2CH_2)_v—(C_gH_{2g})—$;
(iv) $R_fOCFHCF_2O(C_wH_{2w})—$;
(v) $R_fOCF(CF_3)CONH—(C_gH_{2g})—$; or
(vi) $R_f(CH_2)_h[(CF_2CF_2)_i(CH_2CH_2)_j]_k—$
  each $R_f$ is independently $C_cF_{(2c+1)}$;
  c is 2 to about 6, preferably from 2 to 4, more preferably 4;
  d is 1 to about 3, preferably from 1 to 2, more preferably 1;
  g is 1 to 4, preferably from 1 to 3, more preferably 2;
  v is 1 to about 4, preferably from 2 to 3, more preferably 2;
  w is from about 3 to about 12, preferably from 4 to 6, more preferably 4;
  h is 1 to about 6, preferably from 1 to 3, more preferably 2;
  i, j, and k are each independently 1, 2, or 3, or a mixture thereof, preferably 1 or 2, more preferably 1;
  provided that the total number of carbon atoms in group (vi) is from about 8 to about 22;
Y is a linear or branched diradical having olefinic unsaturation of the formula $—C_eH_{(2e-2)}—$ wherein
e is 2 or 3, preferably 2;
R is H or a linear or branched alkyl group $C_bH_{(2b+1)}—$; and
b is from 1 to about 18, preferably from 6 to 18.

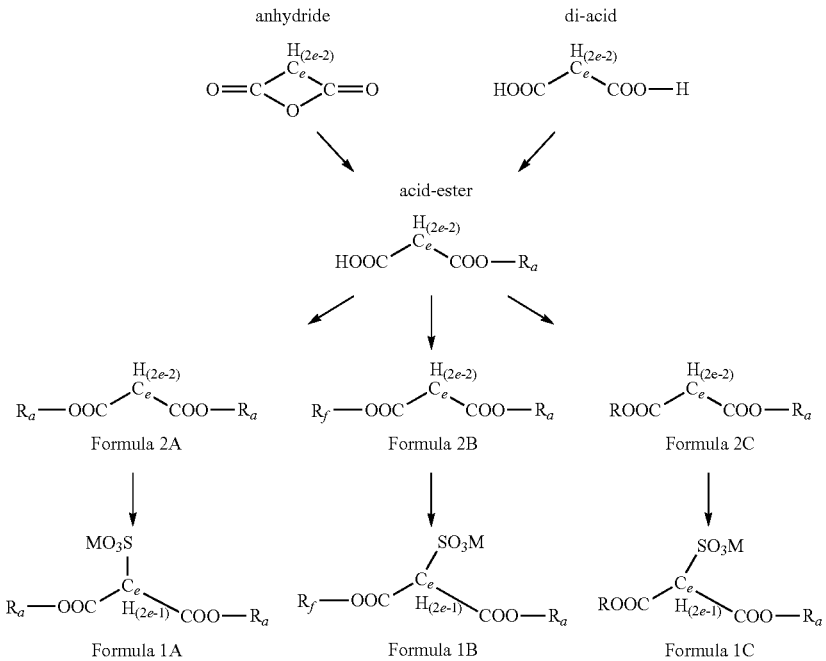

The surfactants of Formula 1A are prepared by reacting two moles of fluoroalcohols of formula $R_a$—OH wherein $R_a$ is defined as above with one mole of an unsaturated linear or branched dibasic acid of the structure $C_eH_{(2e-2)}(COOH)_2$ or its anhydride of Formula D Formula D

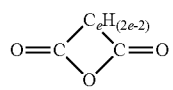

wherein e is 2 or 3 to form the unsaturated diester of Formula 2A as an intermediate. Methods for carboxylic acid esterification are conventional as discussed by Jain and Masse in "Carboxylic acid esters: synthesis from carboxylic acids and derivatives" in Science of Synthesis (2006), 20b, 711-723. An acid catalyst or dehydrating agent is preferred when reacting the free acid groups with alcohols. An example of an acid catalyst is p-toluenesulfonic acid in toluene, and an example of a dehydrating agent is dicyclohexylcarbodiimide in methylene chloride. Preferred unsaturated dibasic acids and corresponding anhydrides are maleic, itaconic (methylenesuccinic acid), citraconic (methylmaleic acid), trans-glutaconic ($HOOCCH_2CH=CHCOOH$), and trans-beta-hydromuconic ($HOOCCH_2CH=CHCH_2COOH$) acids and anhydrides. The unsaturated diester of Formula 2A is then reacted with aqueous sodium hydrogen sulfite to form the sulfonic acid. Sulfonation techniques are described by Roberts in "Sulfonation Technology for Anionic Surfactant Manufacture", Organic Process Research & Development 1998, 2, 194-202, and by Sekiguchi et al. in U.S. Pat. No. 4,545,939. Alternatively, the olefinic precursors described above can be converted to the sulfonates of Formulae 1A, 1B, and 1C by the addition of sulfur trioxide to the double bond. The free sulfonic acid can be used as the surfactant, or the sulfonic acid can be converted to the ammonium salt, the alkali metal salt, or an alkaline earth metal salt, and preferably to the sodium salt. Those skilled in the art will recognize other sulfonation methods, such as those described by Roberts and Sekiguchi (above) are applicable and are included in the present invention.

Addition of the sulfonate group across the double bond of Formulae 1A, 1B, and 1C to make the surfactants of Formulae 2A, 2B, and 2C results in the formation of stereo-isomers and regio-isomers. For the purposes of the present invention, all the isomers are equivalent and all are included in the definitions of Formulae 2A, 2B, and 2C.

The surfactants of Formulae 1B and 1C are prepared by reacting one mole of a fluoroalcohol of formula $R_a$—OH with one mole of an unsaturated linear or branched dibasic acid anhydride of the structure of Formula D at a lower temperature (between about 50-85° C.). The esterification is then continued at a higher temperature (between about 100-120° C.) with a mole of a fluoroalcohol, preferably of formula $R_fCH_2CH_2$—OH, to produce Formula 2B, or a mole of alcohol of formula R—OH, to produce Formula 2C. Any of a variety of conventional fluorinated alcohols are suitable for use at this point of the process. This is followed by conversion to the sulfonates. The anhydride is preferred in the preparation of surfactants of Formulae 1B and 1C. The opening of the anhydride ring by the first esterification is a faster reaction than the second esterification of the intermediate acid ester. As indicated above, in the second esterification acid catalysts or dehydrating agents are used. Use of the dibasic acid thus tends to give mixtures of products. The sequence of use of the two alcohols in the esterifications can be reversed.

The surfactants of Formula 1A can also be prepared using two additions of the same alcohol and the two-temperature procedure described for Formulae 1B and 1C, followed by conversion to the sulfonates. However, this two-step procedure is not preferred.

Mixtures of surfactants of compositions of Formulae 1A, 1B, and 1C can be prepared by using two moles of a mixture of two or more of $R_a$—OH, $R_f$—$CH_2CH_2$—OH, and R—OH alcohols. The two moles of a mixture of two or more alcohols are reacted with one mole of an unsaturated linear or branched dibasic acid of the structure $C_eH_{(2e-2)}(COOH)_2$ or its anhydride (Formula D) as described above for the preparation of surfactants of Formula 1A, followed by conversion to the sulfonates. Such surfactant mixtures can be used as is or separated into the component fractions. Such separations are not preferred.

Alcohols containing the $R_a$ group (i) of $R_f(CH_2CF_2)_q$—$CH_2CH_2$— useful in the invention include the fluorinated telomer alcohols of formula (V):

wherein $R_f$ is a linear or branched perfluoroalkyl group having 2 to 6 carbon atoms, and subscripts q and r are each independently integers of 1 to 3. These telomer alcohols are available by synthesis according to Scheme 1 wherein $R_f$, q and r are as defined for Formula (V).

Scheme 1

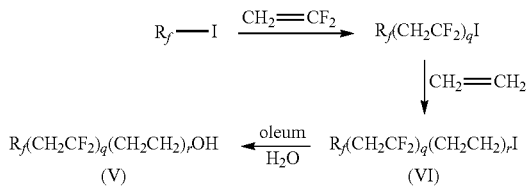

The telomerization of vinylidene fluoride with linear or branched perfluoroalkyl iodides produces compounds of the structure $R_f(CH_2CF_2)_qI$, wherein, q is 1 or more and $R_f$ is a $C_2$ to $C_6$ perfluoroalkyl group. For example, see Balague, et al, "Synthesis of fluorinated telomers, Part 1, Telomerization of vinylidene fluoride with perfluoroalkyl iodides", J. Fluorine Chem. (1995), 70(2), 215-23. The specific telomer iodides are isolated by fractional distillation. The telomer iodides are treated with ethylene by procedures described in U.S. Pat. No. 3,979,469 to provide the telomer ethylene iodides (VI of Scheme 1) wherein r is 1 to 3 or more. The telomer ethylene iodides (VI of Scheme 1) are treated with oleum and hydrolyzed to provide the corresponding telomer alcohols (V of Scheme 1) according to procedures disclosed in WO 95/11877. Alternatively, the telomer ethylene iodides (VI of Scheme 1) can be treated with N-methyl formamide followed by ethyl alcohol/acid hydrolysis.

The $R_a$ group of Formula (ii) $R_fOCF_2CF_2(C_gH_{2g})$—, is obtained by preparing fluoroalcohols of the formula $R_fOCF_2CF_2$—$CH_2CH_2OH$ which are available by the following series of reactions wherein $R_f$ is a linear or branched $C_2$ to $C_6$ perfluoroalkyl optionally interrupted by one to three oxygen atoms and q is an integer of 1 to 3:

Scheme 2

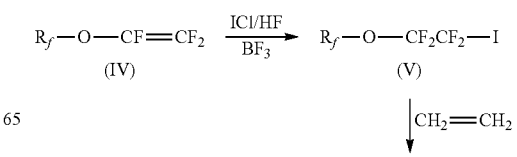

-continued

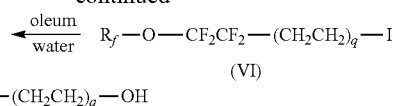

(VI)

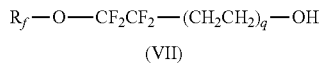

(VII)

The perfluoroalkyl ether iodides of formula (V of Scheme 2) above can be made by the procedure described in U.S. Pat. No. 5,481,028, herein incorporated by reference, in Example 8, which discloses the preparation of compounds of formula (V of Scheme 2) from perfluoro-n-propyl vinyl ether. The perfluoalkyl ether iodide (V of Scheme 2) is reacted with an excess of ethylene at an elevated temperature and pressure. While the addition of ethylene can be carried out thermally, the use of a suitable catalyst is preferred. Preferably the catalyst is a peroxide catalyst such as benzoyl peroxide, isobutyryl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time can vary with the catalyst and reaction conditions, but 24 hours is usually adequate. The product is purified by any means that separates unreacted starting material from the final product, but distillation is preferred. Satisfactory yields up to 80% of theory have been obtained using about 2.7 mols of ethylene per mole of perflualkyl ether iodide, a temperature of 110° C. and autogenous pressure, a reaction time of 24 hours, and purifying the product by distillation.

The perfluoroalkylether ethylene iodides (VI of Scheme 2) are treated with oleum and hydrolyzed to provide the corresponding alcohols (VII of Scheme 2) according to procedures disclosed in WO 95/11877 (Elf Atochem S.A.). Alternatively, the perfluoroalkylether ethyl iodides can be treated with N-methyl formamide followed by ethyl alcohol/acid hydrolysis. A temperature of about 130° to 160° C. is preferred.

The $R_a$ group of Formula (iii), $R_fOCFHCF_2O(CH_2CH_2O)_v$—$(C_gH_{2g})$—, is prepared by reacting a fluorinated vinyl ether with a polyethylene glycol. Typically the vinyl ether is slowly added to the glycol in a molar ratio of from about 1:1 to about 3:1, preferably at about 2:1. The reaction is conducted in the presence of sodium hydride, which is a catalyst that is basic enough to generate equilibrium amounts of the alkoxide anion from the glycol. Other suitable base catalysts include potassium hydride, sodium amide, lithium amide, potassium tert-butoxide, and potassium hydroxide. The reaction is conducted under an inert atmosphere such as nitrogen gas. Suitable solvents include dimethylformamide, dimethylacetamide, acetonitrile, tetrahydrofuran, and dioxane. Preferred is dimethylformamide. Cooling is employed to maintain the reaction temperature at from about 0° C. to about 30° C. The reaction is usually conducted for 1 to about 18 hours. The solvent is then removed using conventional techniques; such as evaporation in vacuum on a rotary evaporator, or in cases where the product is water insoluble and the solvent is water soluble, addition of the mixture to an excess of water followed by separation of the layers.

The reaction of perfluoropropyl vinyl ether with polyethylene glycol does not always go to completion. The average degree of conversion of the polyethylene glycol hydroxyl groups can be determined by $^1$H NMR spectroscopy. Typically mixtures of unreacted polyethylene glycol, the product of fluorinated vinyl ether adding to one end of polyethylene glycol (for example, structure B below), and the product of fluorinated vinyl ether adding to both ends of the polyethylene glycol (for example, structure A below) can be obtained.

The relative amounts of the components of the mixture are affected by the ratio of the reactants, the reaction conditions, and the way in which the product is isolated. High ratios of the vinyl ether to glycol and long reaction times tend to favor Structure A, shown below. Lower ratios of vinyl ether to glycol and shorter reaction times give increased amounts of Structure B, shown below, and unreacted polyethylene glycol. It is sometimes possible to use the differences in solubility between Structures A, B, and the starting glycol to do selective solvent extraction of mixtures to obtain samples that are highly enriched in Structures A or B. The alcohol of Structure B is the required composition for the group $R_a$ (iii).

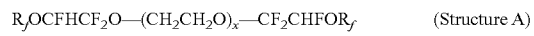 (Structure A)

 (Structure B)

Polyethylene glycols suitable for the use are commercially available from Sigma-Aldrich, Milwaukee, Wis. The fluorinated vinyl ether used in the above reaction is made by various methods. These methods include making fluorinated vinyl ethers by reacting a 2-alkoxypropionyl fluoride in a stationary bed of a metal carbonate, a tubular reactor filled with dried metal carbonate and equipped with a screw blade running through the tube, or a fluidized bed of metal carbonate. US Patent Application 2007/0004938 describes a process to produce fluorinated vinyl ether by reacting a 2-alkoxypropionyl fluoride with a metal carbonate under anhydrous conditions in a stirred bed reactor at a temperature above the decarboxylation temperature of an intermediate carboxylate to produce fluorinated vinyl ether. Examples of fluorinated vinyl ethers suitable for use include $CF_3$—O—$CF=CF_2$, $CF_3CF_2$—O—$CF=CF_2$, $CF_3CF_2CF_2$—O—$CF=CF_2$, and $CF_3CF_2CF_2CF_2$—O—$CF=CF_2$, each of which are available from E. I. du Pont de Nemours and Company, Wilmington, Del.

The $R_a$ group of Formula (iv) $R_fOCFHCF_2O(C_wH_{2w})$—wherein w is from about 3 to about 12, is prepared by the reaction of a perfluorohydrocarbonvinyl ether with a diol in the presence of an alkali metal compound. Preferred ethers include those of formula $R_f$—O—$CF=CF_2$ wherein $R_f$ is a perfluoroalkyl of two to six carbons. The diol is used at about 1 to about 15 mols per mol of ether, preferably from about 1 to about 5 mols per mol of ether. Suitable alkali metal compounds include an alkali metal, alkali earth metal, alkali hydroxide, alkali hydride, or an alkali amide. Preferred are alkali metals such as Na, K or Cs, or alkali hydrides such as NaH or KH. The reaction is conducted at a temperature of from about 40° C. to about 120° C. The reaction can be conducted in an optional solvent, such as ether or nitrile.

The $R_a$ group of Formula (v) $R_fOCF(CF_3)CONH$—$CH_2CH_2$—, is prepared by making a fluorinated alcohol of Formula 4:

Formula 4

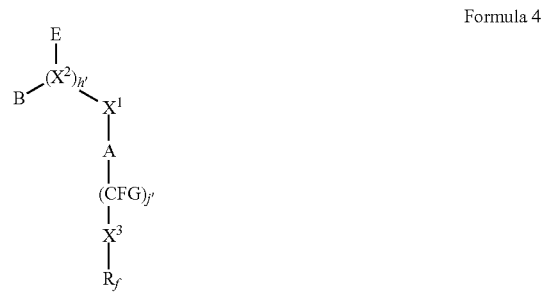

wherein $R_f$ is a straight or branched perfluoroalkyl group having from about 2 to about 6 carbon atoms, or a mixture thereof, $X^3$ is oxygen or $X^1$, each $X^1$ is independently an organic divalent linking group having from about 1 to about 20 carbon atoms, optionally containing an oxygen, nitrogen, or sulfur, or a combination thereof, G is F or $CF_3$, A is an amide, j' is zero or positive integer, $X^2$ is an organic linking group, h' is zero or one, B is H, and E is hydroxyl.

The compound of Formula 4 is prepared by reaction between a perfluorinated ester (prepared according to reported methods in U.S. Pat. No. 6,054,615 and U.S. Pat. No. 6,376,705 each herein incorporated by reference) with a triamine or diamine alcohol with or without solvent. The conditions of this reaction are dependent on structure of the ester. The reaction of alpha, alpha-difluorosubstituted ester with diamine is conducted at a temperature of from about 5° C. to about 35° C. Suitable solvents for this reaction include tetrahydrofuran, methyl isobutyl ketone, acetone, $CHCl_3$, $CH_2Cl_2$, or ether. The reaction of ester without alpha-fluorine substitution with diamine is conducted at a temperature of from about 90° C. to about 160° C., preferably at between about 100° C. to about 140° C. Preferably no solvent is employed for this reaction, but suitable solvents include chlorobenzene, dimethylformamide, or 2-methoxyethyl ether.

The compound of Formula 4 is also prepared by reaction between a perfluorinated acyl fluoride with a diamine alcohol or amine alcohol. This reaction is conducted at a temperature of from about −30° C. to about 40° C., preferably at between about 5° C. to about 25° C. Suitable solvents for this reaction include tetrahydrofuran, methyl isobutyl ketone, acetone, $CHCl_3$, $CH_2Cl_2$, or 2-methoxyethyl ether, diethyl ether.

The $R_a$ group of Formula (vi), above, $R_f(CH_2)_h[(CF_2CF_2)_i(CH_2CH_2)_j]_k$—, is obtained by preparation of fluoroalcohols of the formula $R_f(CH_2)_h[(CF_2CF_2)_i(CH_2CH_2)_j]_kOH$, wherein $R_f$ is a $C_2$ to $C_6$ perfluoroalkyl, subscript h is 1 to about 6, and subscripts i, j, and k are each independently 1, 2, 3, or a mixture thereof. These alcohols are prepared from oligomeric iodides ($C_nF_{2n+1}C_2H_4I$, $C_nF_{2n+1}CH_2I$ or $C_nF_{2n+1}I$) wherein subscript n is an integer from 1 to about 6, using an oleum treatment and hydrolysis. It has been found, for example, that reacting with oleum (15% $SO_3$) at about 60° C. for about 1.5 hours, followed by hydrolysis using an iced dilute $K_2SO_3$ solution, and then followed by heating to about 100° C. for about 30 minutes gives satisfactory results. But other reaction conditions can also be used. After being cooled to ambient room temperature, a solid is precipitated, isolated and purified. For example, the liquid is then decanted and the solid is dissolved in ether and washed with water saturated with NaCl, dried over anhydrous $Na_2SO_4$, and concentrated and dried under vacuum. Other conventional purification procedures can be employed.

Alternatively, the alcohols of formula $R_f(CH_2)_h[(CF_2CF_2)_i(CH_2CH_2)_j]_kOH$ as defined above can be prepared by heating the oligomeric iodides $R_f(CH_2)_h[(CF_2CF_2)_i(CH_2CH_2)_j]_kI$ wherein $R_f$, and subscripts h, i, j, and k are as defined above for the corresponding alcohol, with N-methylformamide to about 150° C. and holding for about 19 hours. The reaction mixture is washed with water to give a residue. A mixture of this residue with ethanol and concentrated hydrochloric acid is gently refluxed (at about 85° C. bath temperature) for about 2.5 hours. The reaction mixture is washed with water, diluted with dichloromethane, and dried over sodium sulfate. The dichloromethane solution is concentrated and distilled at reduced pressure to give the alcohol. Optionally N,N-dimethylformamide can be used instead of N-methylformamide. Other conventional purification procedures can also be employed.

The iodides of formula $R_f(CH_2)_h[(CF_2CF_2)_i(CH_2CH_2)_j]_kI$ are preferably prepared by oligomerization of $C_nF_{2n+1}C_2H_4I$, $C_nF_{2n+1}CH_2I$ or $C_nF_{2n+1}I$ wherein n is 1 to about 6 using a mixture of ethylene and tetrafluoroethylene. The reaction can be conducted at any temperature from room temperature to about 150° C. with a suitable radical initiator. Preferably the reaction is conducted at a temperature of from about 40° to about 100° C. with an initiator which has about a 10 hour half-life in that range. The feed ratio of the starting materials in the gas phase, that is the moles of $C_nF_{2n+1}C_2H_4I$, $C_nF_{2n+1}CH_2I$ or $C_nF_{2n+1}I$ wherein n is 1 to about 6, versus the combined moles of ethylene and tetrafluoroethylene, can be used to control conversion of the reaction. This mole ratio is from about 1:3 to about 20:1, preferably from about 1:2 to 10:1, more preferably from about 1:2 to about 5:1 The mole ratio of ethylene to tetrafluoroethylene is from about 1:10 to about 10:1, preferably from about 3:7 to about 7:3, and more preferably from about 4:6 to about 6:4.

The present invention further comprises the unsaturated intermediates used in the preparation of the surfactants of the present invention that are formed prior to the addition of the sulfonic acid group. The unsaturated intermediates have the structure of Formulae 2A, 2B, and 2C:

  Formula 2A (R_a—O—CO—)_2Y

  Formula 2B

R_a—O—CO—Y—CO—O—(CH_2CH_2)R_f

  Formula 2C

R_a—O—CO—Y—CO—O—R wherein $R_a$ is the group (i) $R_f(CH_2CF_2)_d$—$(C_gH_{2g})$—;

(ii) $R_fOCF_2CF_2$—$(C_gH_{2g})$—;

(iii) $R_fOCFHCF_2O(CH_2CH_2O)_v$—$(C_gH_{2g})$—;

(iv) $R_fOCFHCF_2O(C_wH_{2w})$—;

(v) $R_fOCF(CF_3)CONH$—$(C_gH_{2g})$—; or (vi) $R_f(CH_2)_h[(CF_2CF_2)_i(CH_2CH_2)_j]_k$ each $R_f$ is independently $C_cF_{(2c+1)}$;

c is 2 to about 6, preferably from 2 to 4, more preferably 4;

d is 1 to about 3, preferably from 1 to 2, more preferably 1;

g is 1 to 4, preferably from 1 to 3, more preferably 2;

v is 1 to about 4, preferably from 2 to 3, more preferably 2;

w is from about 3 to about 12, preferably from 4 to 6, more preferably 4;

h is 1 to about 6, preferably from 1 to 3, more preferably 2;

i, j, and k are each independently 1, 2, or 3, or a mixture thereof, preferably 1 or 2, more preferably 1;

provided that the total number of carbon atoms in group (vi) is from about 8 to about 22;

Y is a linear or branched diradical having olefinic unsaturation of the formula

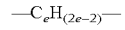

—$C_eH_{(2e-2)}$— wherein e is 2 or 3, preferably 2;

R is H or a linear or branched alkyl group $C_bH_{(2b+1)}$—; and b is from 1 to about 18, preferably from 6 to 18.

Compounds of Formulae 2A, 2B, and 2C are prepared as discussed above for Formulae 1A, 1B, and 1C except that the sulfonation step is omitted. Compounds of Formula 2A, 2B, and 2C are also monomers that can be polymerized alone or in admixture with other monomers to confer soil and water repellency to the resulting polymers and to surfaces to which the resulting polymers are applied.

Preferred compounds of Formula 2A, 2B, and 2C are those wherein $R_a$ is $R_f(CH_2CF_2)_d$—$(C_gH_{2g})$—; $R_fOCF_2CF_2$—$(C_gH_{2g})$—; $R_f$—$OCFHCF_2O(CH_2CH_2O)_v$—$(C_gH_{2g})$—; or $R_fOCFHCF_2O(C_wH_{2w}O)$—$(C_gH_{2g})$—. Also preferred are those compounds of Formula 2A, 2B and 2C wherein c is 3 or 4, or wherein Y is CH=CH, $CH_2C(=CH_2)$, $C(CH_3)=CH_2$, CH=CHCH$_2$, or $CH_2CH=CHCH_2$. More preferred are those compounds wherein $R_a$ is $R_f(CH_2CF_2)_d$—$(C_gH_{2g})$—; $R_fOCF_2CF_2$—$(C_gH_{2g})$—; $R_fOCFHCF_2O(CH_2CH_2O)_v$—$(C_gH_{2g})$—; or $R_fOCFHCF_2O(C_wH_{2w}O)$—$(C_gH_{2g})$—; d is 1, g is 1, $R_f$ is $C_3F_7$ or $C_4F$, and Y is CH=CH, $CH_2C(=CH_2)$, or $C(CH_3)=CH_2$. Also preferred are compounds of Formula 2B wherein $R_a$ is $C_4F_9CH_2CF_2CH_2CH_2$ or $C_3F_7CH_2CF_2CH_2CH_2$ and $R_f$ is $(CF_2)_6F$.

The compounds of Formula 2A, 2B and 2C are useful as intermediates to prepare partially fluorinated sulfonated surfactants, in particular those of Formula 1A, 1B and 1C as previously defined.

The present invention further comprises a method of altering the surface behavior of a liquid, comprising adding to the liquid a compound of Formulae 1A, 1B, and 1C, as defined above, in a wide variety of applications. The surfactants of Formula 1A, 1B, and 1C are typically used by simply blending with or adding to water, aqueous solutions, and aqueous emulsions. The surfactants of Formulae 1A, 1B, and 1C typically lower surface and interfacial tensions and provide low critical micelle concentrations. Examples of surface behavior alteration include improvements in the properties of wetting, penetration, spreading, leveling, flowing, emulsifying, stabilization of dispersions in liquids, repellency, releasing, lubricating, etching, and bonding.

Examples of such applications where low surface tension is required include coating compositions and aqueous and non-aqueous cleaning products, each for glass, wood, metal, brick, concrete, cement, natural and synthetic stone, tile, synthetic flooring, laminates, paper, textile materials, linoleum and other plastics, resins, natural and synthetic rubbers, fibers and fabrics, and paints; polymers; and waxes, finishes, leveling and gloss agents for floors, furniture, shoes, inks, and automotive care. Wetting agent applications include wetting agents for compositions containing herbicides, fungicides, weed killers, hormone growth regulators, parasiticides, insecticides, germicides, bactericides, nematocides, microbiocides, defoliants or fertilizers, therapeutic agents, antimicrobials, fluorochemical blood substitutes, textile treatment baths, and fiber spin finishes. Applications in personal care products include shampoos, conditioners, creme rinses, cosmetic products for the skin (such as therapeutic or protective creams and lotions, oil and water repellent cosmetic powders, deodorants and antiperspirants), nail polish, lipstick, and toothpaste. Further applications include fabric care products (such as stain pretreatments and/or stain removers for clothing, carpets and upholstery), and laundry detergents. Other applications include rinse-aids (for car washes and in automatic dishwashers), for oil well treatments (including drilling muds and additives to improve tertiary oil well recovery), extreme pressure lubricants, lubricating cutting oil to improve penetration times, writing inks, printing inks, photography developer solutions, emulsions for fighting forest fires, dry chemical fire extinguishing agents, aerosol-type fire extinguishers, thickening agents to form gels for solidifying or encapsulating medical waste, photoresists, developers, cleaning solutions, etching compositions, developers, polishers, and resist inks in the manufacturing, processing, and handling of semiconductors and electronics. The surfactants of the present invention can be incorporated into products that function as antifogging agents for glass surfaces and photography films, and as antistatic agents for magnetic tapes, phonograph records, floppy disks, disk drives, rubber compositions, PVC, polyester film, and photography films, and as surface treatments for optical elements (such as glass, plastic, or ceramics). Other applications are in emulsifying agents, foaming agents, release agents, repellency agents, flow modifiers, film evaporation inhibitors, wetting agents, penetrating agents, cleaners, grinding agents, electroplating agents, corrosion inhibitors, soldering agents, dispersion aids, microbial agents, pulping aids, rinsing aids, polishing agents, drying agents, antistatic agents, antiblocking agents, bonding agents, and oil field chemicals.

The compounds of the present invention are also useful as foam control agents in polyurethane foams, spray-on oven cleaners, foamed kitchen and bathroom cleansers and disinfectants, aerosol shaving foams, and in textile treatment baths. The surfactants of the present invention are useful as emulsifying agents for polymerization, particularly of fluoromonomers, as latex stabilizers, as mold release agents for silicones, photoemulsion stabilizers, inorganic particles, and pigments. Such fluorosurfactants are also useful for supercritical carbon dioxide emulsions and dispersion of nanoparticles or pigments in water.

A low concentration of less than about 0.1%, preferably less than about 0.01% by weight of a compound of Formulae 1A, 1B, or 1C in the liquid is effective. Consequently, the surfactants of Formulae 1A, 1B, and 1C are useful in a wide variety of end use applications.

The present invention further comprises compounds of Formula 5

$R_fOCFHCF_2O(CH_2CH_2O)_v$—H    Formula 5 wherein
$R_f$ is $C_cF_{(2c+1)}$;
c is 2 to about 6, preferably from 2 to 4, more preferably 4; and
v is 2 to about 4, preferably from 2 to 3, more preferably 2.

Preferred compounds of Formula 5 are those wherein c is 3 or 4, g is 2, and v is 2 or 3. The compounds of Formula 5 are useful as intermediates in making partially fluorinated sulfonated surfactants. In particular, Formula 5 compounds are useful in making surfactants of Formula 1A, 1B and 1C as previously defined.

The present invention further comprises a process for the preparation of a compound of Formula 5

$R_fOCFHCF_2O(CH_2CH_2O)_v$—H    Formula 5 wherein
$R_f$ is $C_cF_{(2c+1)}$;
c is 2 to about 6; and
v is 2 to about 4,
comprising contacting a compound of Formula 6

$R_f$—O—CF=CF$_2$    Formula 6 wherein $R_f$ is $C_cF_{(2c+1)}$, and c is 2 to about 6, with a compound of Formula 7

HO—$(CH_2CH_2O)_v$—H    Formula 7 wherein v is 2 to about 4.

In the process of the present invention the compound of Formula 5 is prepared by the reaction of a perfluorohydrocarbonvinyl ether with a diol in the presence of an alkali metal compound. Preferred ethers include those of formula $R_f$—O—CF=CF$_2$ wherein $R_f$ is a perfluoroalkyl of one to six carbons. Preferred diols include diethylene glycol. The diol is used at about 1 to about 15 mols per mol of ether, preferably from about 1 to about 5 mols per mol of ether. Suitable alkali metal compounds include an alkali metal, alkali earth metal, alkali hydroxide, alkali hydride, or an alkali amide. Preferred are alkali metals such as Na, K or Cs or alkali hydrides such as NaH or KH. The reaction is conducted at a temperature of from about ambient temperature to about 120° C., preferably from about 40° C. to about 120° C. The reaction can be conducted in an optional solvent, such as ether or nitrile. The process is useful to prepare alcohols of Formula 5 which are used to prepare derivative compounds, such as surfactants.

The surfactants of the present invention of Formula 1A, 1B, and 1C, in many cases, require less tetrafluoroethylene in their preparation when compared to conventional fluorosurfactants made from Telomer B alcohols. While tetrafluoroethylene may be used in the $R_f$ portion of the $R_a$—OH alcohol precursors when $R_a$ is (ii) $R_fOCF_2CF_2$—$(C_gH_{2g})$—; (iii) $R_fOCFHCF_2O(CH_2CH_2O)_v$—$(C_gH_{2g})$—; (iv) $R_fOCFHCF_2O(C_wH_{2w})$—; or (v) $R_fOCF(CF_3)CONH$—$(C_gH_{2g})$; tetrafluoroethylene is not otherwise used in the preparation of the compounds of Formula 1A, 1B or 1C or of Formula 2A, 2B or 2C. For the surfactants of the present invention, some of the fluorine is replaced with other atoms or monomers, compared to the typical perfluoroalkyl groups of 1 to 20 carbons in surfactants made from traditional Telomer B alcohols. So less tetrafluoroethylene is used in the preparation of compounds of Formula 1A, 1B and 1C or of Formula 2A, 2B and 2C containing the $R_a$ (i) and (vi) groups.

The monomer moieties replacing tetrafluoroethylene in most cases also contain a lower proportion of fluorine. Consequently, in many cases the surfactants of the present invention are more fluorine efficient than many conventional surfactants. By "fluorine efficiency" is meant the ability to use a minimum amount of fluorochemical to obtain a desired surface effect or surfactant properties, when applied to substrates, or to obtain better performance using the same level of fluorine.

MATERIALS AND TEST METHODS

The following materials and test methods were used in the Examples herein.

All common organic and inorganic compounds were obtained from Sigma-Aldrich (Milwaukee Wis.) and used without purification. These included maleic anhydride, sodium hydrogen sulfite, toluene, hexane, p-toluene sulfonic acid, itaconic anhydride, citraconic anhydride, trans-glutaconic acid, trans-beta-hydromuconic acid, and other routine compounds employed in the Examples.

SIMULSOL SL8: octyl/deceyl polyglucoside is available from Kreglinger Europe, Antwerp, Belgium.

TRITON X100: p-tert-octylphenoxy polyethyl alcohol is available from Sigma-Aldrich, Saint Louis, Mo.

DOWANOL DB: 1-butoxy-2-ethoxyethane is available from Dow Chemical Company, Midland, Mi.

SOLKANE 365 MFC is 1,1,1,3,3-pentafluorobutane is available from Solvay Fluorides, Thorofare N.J.

The following fluorinated chemicals are available from E. I. du Pont de Nemours and Company, Wilmington Del.:
Perfluoro-2-methyl-3-oxahexanoyl fluoride,
Perfluorobutyl iodide,
Vinylidene fluoride,
Perfluoropropylvinyl ether, and
Perfluoroethylethyl iodide.

The following fluorinated chemicals were prepared as indicated below:

$C_4F_9CH_2CF_2I$ and $C_4F_9(CH_2CF_2)_2I$ were prepared by reacting perfluorobutyl iodide and vinylidene fluoride as described by Balague, et al, "Synthesis of Fluorinated Telomers, Part 1, Telomerization of Vinylidene Fluoride with Perfluoroalkyl Iodides", J. Fluorine Chem. (1995), 70(2), 215-23. The specific telomer iodides are isolated by fractional distillation.

$C_3F_7OCF_2CF_2I$ was prepared by reacting perfluoropropyl vinyl ether with iodine chloride and hydrofluoric acid with boron trifluoride as a catalyst as described by Viacheslav et al. in U.S. Pat. No. 5,481,028.

Test Method 1—Measurement of the Critical Micelle Concentration (CMC) and the Surface Tension Beyond CMC.

Surface tensions of aqueous surfactant solutions were measured at various weight percents in mN/m using a Kruss K11 Tensiometer (from Kruss USA, Charlotte, N.C.). Compounds having the lowest surface tension have the highest effectiveness.

The critical micelle concentration (CMC) is defined as the concentration at which increased concentrations of surfactant essentially no longer reduce the surface tension. To determine CMC, the surface tension is measured as a function of surfactant concentration. Surface tension is then plotted (abscissa) vs. log concentration (ordinate). The resulting curve has a nearly horizontal portion at concentrations higher than the CMC and has a negative steep slope at concentrations less than the CMC. The CMC is the concentration at the intersection of the extrapolated steep slope and the extrapolated near horizontal line. The Surface Tension beyond CMC is the value in the flat portion of the curve. The CMC should be as low as possible to provide the lowest cost for effective performance.

Test Method 2—Spreading on Cyclohexane

Test Method 2 is adapted from Stern et al. in WO1997046283A1, wherein surfactants were applied to the surface of n-heptane to provide a screening evaluation for Advance Fire Fighting Foams (AFFF). Cyclohexane was used in Test Method 2 to replace the n-heptane used by Stern et al. Test Method 2 measures the ability of the surfactant solution to spread across the surface of a less dense flammable liquid. When the surfactant solution spreads across the surface ("excellent" rating), a barrier is established between the flammable liquid and the air. If the surfactant solution does not spread completely across the surface ("good" or "fair" rating depending on the extent of the partial spreading) the barrier between air and flammable liquid is incomplete. If the surfactant solution sinks into the flammable liquid ("poor" rating), no barrier between air and flammable liquid is established.

A surfactant solution was prepared by combining fluorosurfactant (0.9 g/L of active ingredient), hydrocarbon surfactant (either SIMULSOL SL8 or TRITON X100; 2.4 g/L of active ingredient), butyl carbitol (DOWANOL DB; 4.2 g/L of active ingredient), and mixed thoroughly. A Petri dish (11.5 cm diameter) was filled about half-way with 75 mL of cyclohexane. After the surface of the cyclohexane had completely calmed (about 1 minute), 100 microliters of the solution of fluorosurfactant, hydrocarbon surfactant, butyl carbitol, and water was deposited dropwise with a micropipette beginning at the center of the Petri dish and outwardly along a radial line to the outer edge of the Petri dish. The timer was started.

In poor performing formulations, the surfactant solution "sinks immediately" below the cyclohexane.

In fair performing formulations, the surfactant solution merely "floats" on the surface of the cyclohexane without sinking.

In good performing formulations, the surfactant spreads across the surface of the cyclohexane. The time was noted when the extent of the spreading of the surfactant solution across the surface of the cyclohexane ceased and the extent of the surface coverage (<100%) at that point was recorded.

In excellent performing formulations, the surfactant solution rapidly spreads across the entire surface of the cyclohexane. In excellent performing formulations, the time was noted when extent of the spreading of the surfactant solution first covered the entire surface (100%).

EXAMPLES

Compound 1

A mixture of ethanolamine (13 g, 28 mmol) and ether (30 mL) was cooled to 15° C. Perfluoro-2-methyl-3-oxahexanoyl fluoride (33 g in ether 50 mL) was added dropwise to keep the reaction temperature below 25° C. After the addition, the reaction mixture was stirred at room temperature for one hour. The solid was removed by filtration and the filtrate was washed with hydrochloric acid (0.5N, 30 mL), water (2 times 30 mL), sodium hydrogen carbonate solution (0.5N, 20 mL), water (30 mL), and sodium chloride solution (saturated, 20 mL). It was then concentrated and dried in vacuum over night at room temperature to give a white solid 35 g, yield 95%. The product was analyzed using $^1$HNMR and the structure confirmed as is N-(perfluoro-2-methyl-3-oxahexanoyl)-2-aminoethanol, $C_3F_7OCF(CF_3)CONHCH_2CH_2OH$.

A mixture of maleic anhydride (0.60 g, 6.1 mmol), $C_3F_7OCF(CF_3)CONHCH_2CH_2OH$ (4.5 g, 12 mmol, prepared as described above), p-toluenesulfonic acid monohydrate (0.12 g) and toluene (50 mL) was stirred continuously and heated to reflux under nitrogen. The temperature was maintained at 111° C. for approximately 22 h until 90% of water was removed azeotropically with the aid of a Dean-Stark trap. A liquid chromatography/mass spectrum (LC/MS) was taken to show the completion to the diester. The solution was separated and extracted with two washings of 5% sodium bicarbonate solution. The combined organic extracts were dried over anhydrous magnesium sulfate ($MgSO_4$) and then toluene was removed by rotary evaporation. The yellow oil (3.12 g, 61.9% yield, 90% purity) was analyzed by $^1$HNMR and LC/MS to confirm the structure as $C_3F_7OCF(CF_3)C(O)NHCH_2CH_2OC(O)CH=CHC(O)OCH_2CH_2NHC(O)-CF(CF_3)OC_3F_7$.

Compound 2

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$ by 54-57° C. at 2 mmHg (267 Pa).

The esterification procedure of Example 1 was used to make Di(1H,1H,2H,2H,4H,4H-perfluorooctyl)maleate (7.76 g, 95% yield, 95% purity) by the reaction of maleic anhydride (1.07 g, 11 mmol). $C_4F_9CH_2CF_2CH_2CH_2OH$ (7.13 g, 22 mmol, prepared as described above) and p-toluenesulfonic acid monohydrate (0.21 g, 1.1 mmol) in 50 mL of toluene at 111° C. for 40 h. The pale yellow product was analyzed by $^1$HNMR and LC/MS to confirm the structure as $C_4F_9CH_2CF_2CH_2CH_2OC(O)-CH=CH-C(O)OCH_2CH_2CF_2CH_2C_4F_9$.

Compound 3

Ethylene (56 g) was introduced to an autoclave charged with $C_4F_9(CH_2CF_2)_2I$ (714 g) and d-(+)-limonene (3.2 g), and the reactor heated at 240° C. for 12 hours. The product was isolated by vacuum distillation to provide $C_4F_9(CH_2CF_2)_2CH_2CH_2I$. A mixture of $C_4F_9(CH_2CF_2)_2CH_2CH_2I$ (10 g, 0.02 mol) and N-methylformamide (8.9 mL, 0.15 mol) was heated to 150° C. for 26 hours. The mixture was cooled to 100° C., followed by the addition of water to separate the crude ester. Ethyl alcohol (3 mL) and p-toluene sulfonic acid (0.09 g) were added and the mixture stirred at 70° C. for 0.25 hours. Ethyl formate and ethyl alcohol were removed by distillation to give a crude product. The crude product was dissolved in ether, washed with 10 wt % aqueous sodium sulfite, water and brine, in turn, and dried over magnesium sulfate. Distillation provided the product $C_4F_9(CH_2CF_2)_2CH_2CH_2OH$ (6.5 g, 83% yield): by 94-95° C. at 2 mm Hg (266 Pa).

Maleic anhydride (0.65 g, 6.7 mmol), $C_4F_9CH_2CF_2CH_2CF_2CH_2CH_2OH$ (4.37 g, $1.333*10^{-2}$ mol, prepared as described above), p-toluenesulfonic acid monohydrate (0.13 g, 0.67 mmol) and toluene (50 mL) were mixed together and heated to reflux at 110° C. for 48 h. The work-up was carried out as in Example 1. The resulting pale yellow liquid (2.90 g, 51.4% yield, >99% purity) was analyzed by $^1$H NMR and LC/MS to confirm the structure as $C_4F_9CH_2CF_2CH_2CF_2CH_2CH_2OC(O)CH=CH-C(O)OCH_2CH_2CF_2CH_2CF_2CH_2C_4F_9$.

Compound 4

$C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56~60° C. at 25 mm Hg (3.3 kPa).

A mixture of $C_3F_7OCF_2CF_2CH_2CH_2I$ (300 g, 0.68 mol, prepared as described above) and N-methyl-formamide (300 mL), was heated to 150° C. for 26 h. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of $C_3F_7OCF_2CF_2CH_2CH_2OH$ in 85% yield. The boiling point was 71~73° C. at 40 mm Hg (5333 Pa).

A similar procedure as Example 1 was conducted. Maleic anhydride (0.66 g, 6.8 mmol), $C_3F_7OCF_2CF_2CH_2CH_2OH$ (4.46 g, 14 mmol, prepared as described above), p-toluenesulfonic acid monohydrate (0.13 g, 0.68 mmol) and toluene (50 mL) were mixed together and refluxed for 50 h at 112° C.

The pale yellow crude product (4.12 g, 82.4%, >99% purity) was analyzed by $^1$H NMR and LC/MS to confirm the structure as $C_3F_7OCF_2CF_2CH_2CH_2OC(O)CH=CHC(O)OCH_2CH_2NHC(O)CF(CF_3)OC_3F_7$.

Compound 5

In a dry box, a 500 mL Pyrex bottle was charged with diethylene glycol (99%, Aldrich Chemical Company) (175 mL, 1.84 mole) and 80 mL of anhydrous tetrahydrofuran (Aldrich Sure/Seal™). NaH (3.90 g, 0.163 mole) was added slowly with magnetic stirring until the completion of hydrogen evolution. The capped bottle was removed from the drybox, and the solution was transferred to a 400 mL metal shaker tube in a nitrogen filled glovebag. The shaker tube was cooled to an internal temperature of −18° C., shaking was started, and perfluoropropylvinyl ether (PPVE, 41 g 0.145 mole) was added from a metal cylinder. The mixture was allowed to warm to room temperature and was shaken for 20 h. The reaction mixture was combined with a duplicate reaction run in a separate 400 mL shaker tube. The combined reaction mixtures were added to 600 mL of water, and this mixture was extracted with 3×200 mL of diethyl ether in a separatory funnel. The ether extracts were dried over $MgSO_4$, filtered, and concentrated in vacuo on a rotary evaporator to give a liquid (119.0 g) $^1$H NMR in $CD_3OD$, and analysis by gas chromatography both showed a small amount of diethylene glycol. This material was dissolved in 150 mL of diethyl ether and extracted with water (3×150 mL) in a separatory funnel. The ether layer was dried over $MgSO_4$, filtered, and concentrated in vacuo on a rotary evaporator at high vacuum to give a liquid (99.1 g) $^1$H NMR($C_6D_6$, ppm downfield of TMS) shows 97 mole % desired mono-PPVE adduct: 1.77 (broad s, OH), 3.08-3.12 (m, $OCH_2CH_2OCH_2CH_2OH$), 3.42 (t, $OCH_2CH_2OCH_2CH_2OH$), $\overline{3.61}$ (t, $OCH_2CH_2OCH_2CH_2OH$), 5.$\overline{496}$ (doublet of triplets, $^2J_{H\text{-}F}$=53 Hz, $^3J_{H\text{-}F}$=3 Hz $OCF_2CHFOC_3F_7$), and 3 mole % of the bis PPVE adduct: 5.470 (doublet of triplets, $^2J_{H\text{-}F}$=53 Hz, $^3J_{H\text{-}F}$=3 Hz, $C_3F_7OCHFCF_2OCH_2CH_2OCH_2CH_2OCF_2CHFOC_3F_7$) The other peaks for the bis PPVE adduct overlap with the mono PPVE adduct.

A mixture of maleic anhydride (0.59 g, 6.1 mmol), $C_3F_7OCHFCF_2OCH_2CH_2OCH_2CH_2OH$ (4.5 g, 12 mmol, prepared as above, p-toluenesulfonic acid monohydrate (0.12 g, 0.61 mmol) and toluene (50 mL) were stirred continuously together and heated to reflux at 114° C. for a period of 25 h. The reaction was confirmed to be completed through LC/MS and the removal of water. The work-up as in Example 1 was carried out to produce a pale yellow liquid (4.48 g, 90.0% yield, 87% purity. $^1$H NMR and LC/MS were used to confirm the complete conversion to the diester and the structure as $C_3F_7OCFHCF_2OCH_2CH_2OCH_2CH_2OC(O)CH=CHC(O)OCH_2CH_2O—CH_2CH_2OCF_2CFHOC_3F_7$.

Compound 6

A one-gallon reactor was charged with perfluoroethylethyl iodide (850 g). After cool evacuation, ethylene and tetrafluoroethylene in a ratio of 27:73 were added until pressure reached 60 psig (414 kPa). The reaction was then heated to 70° C. More ethylene and tetrahydrofuran in a 27:73 ratio were added until pressure reached 160 psig (1.205 MPa). A lauroyl peroxide solution (4 g lauroyl peroxide in 150 g perfluoroethylethyl iodide) was added at a 1 mL/min. rate for 1 hour. Gas feed ratio was adjusted to 1:1 of ethylene and tetrafluoroethylene and the pressure was kept at 160 psig (1.205 MPa). After about 67 g of ethylene was added, both ethylene and tetrafluoroethylene feeds were stopped. The reaction was heated at 70° C. for another 8 hours. The volatiles were removed by vacuum distillation at room temperature. A solid of oligomer ethylene-tetrafluoroethylene iodides $C_2F_5(CH_2)_2[(CF_2CF_2)(CH_2CH_2)]_k$—I (773 g) wherein k is a mixture of 2 and 3 in about a 2:1 ratio was obtained.

An oligomer iodide mixture, prepared as described above (46.5 g) without separation of the iodides was mixed with N-methylformamide (NMF, 273 mL) and heated to 150° C. for 19 h. The reaction mixture was washed with water (4×500 mL) to give a residue. A mixture of this residue, ethanol (200 mL), and concentrated hydrochloric acid (1 mL) was gently refluxed (85° C. bath temperature) for 24 h. The reaction mixture was poured into water (300 mL). The solid was washed with water (2×75 mL) and dried under vacuum (2 torr, 267 Pa) to give a solid, 24.5 g. About 2 g of product was sublimed. The total yield of oligomer alcohols $C_2H_5(CH_2)_n$ $[(CF_2CF_2)(CH_2CH_2)]_k$—OH wherein k is a mixture of 2 and 3 in about a 2:1 ratio was 26.5 g.

A mixture of maleic anhydride (1.74 g, 18 mmol) and $C_2F_5(CH_2)_2[(CF_2CF_2)(CH_2CH_2)]_k$—OH (6.26 g) were stirred continuously together and heated to 70° C. The reaction was carried out neat for 45 h and a gas chromatogram (GC) was taken at several intervals to notice the disappearance of reactants and the introduction of the half acid/ester. $C_2F_5CH_2CH_2[(CF_2CF_2)(CH_2CH_2)]_k$—OC(O)CH=CHC(O)OH. The half acid/ester (4.75 g, 9.7 mmol), $C_2F_5CH_2CH_2[(CF_2CF_2)(CH_2CH_2)]_k$—OH (3.80 g, 9.7 mmol), and p-toluenesulfonic acid monohydrate (0.12 g, 0.97 mmol) were heated to reflux in toluene (50 mL) at 114° C. for 19 h. The product was isolated using extraction with $CH_3CN$ (3×100 mL), concentration, extraction with tetrahydrofuran, concentration, and drying was to produce the yellow/orange solid product (7.46 g, 93.3% yield, 97%), which was analyzed by $^1$H NMR and LC/MS to confirm the structure as $C_2F_5CH_2CH_2[(CF_2CF_2)(CH_2CH_2)]_{kO}OC(O)CH=CHC(O)O[(CH_2CH_2)—(CF_2CF_2)]_k$—$CH_2CH_2C_2F_5$ wherein k is a mixture of 2 and 3.

Compound 7

A mixture of ethanolamine (13 g, 28 mmol) and ether (30 mL) was cooled to 15° C. Perfluoro-2-methyl-3-oxahexanoyl fluoride (33 g in ether 50 mL) was added dropwise to keep the reaction temperature below 25° C. After the addition, the reaction mixture was stirred at room temperature for one hour. The solid was removed by filtration and the filtrate was washed with hydrochloric acid (0.5N, 30 mL), water (2 times 30 mL), sodium hydrogen carbonate solution (0.5N, 20 mL), water (30 mL), and sodium chloride solution (saturated, 20 mL). It was then concentrated and dried in vacuum over night at room temperature to give a white solid 35 g, yield 95%. Analysis by $^1$H NMR and F NMR showed the product was N-(perfluoro-2-methyl-3-oxahexanoyl)-2-aminoethanol, $C_3F_7OCF(CF_3)CONHCH_2CH_2OH$.

Itaconic anhydride (0.67 g, 6.0 mmol), $C_3F_7OCF(CF_3)CONHCH_2CH_2OH$ (4.44 g, 12 mmol, prepared as described above), p-toluenesulfonic acid monohydrate (0.11 g, 0.60 mmol), and toluene (50 mL) were stirred continuously and heated to reflux at 111° C. for a period of 25 h. The toluene was decanted off to leave a yellow, viscous solid. The product was firstly air-dried and then placed in a vacuum oven for 2 h. The product (3.62 g, 72.4%, 65% purity) was analyzed by $^1$H NMR and LC/MS to confirm complete conversion and the structure as $C_3F_7OCF(CF_3)C(O)NHCH_2CH_2OC(O)CH_2C$
$(=CH_2)C(O)OCH_2CH_2-NHC(O)CF(CF_3)OC_3F_7$.

Compound 8

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$ by 54-57° C. at 2 mmHg (267 Pa).

Itaconic anhydride (0.75 g, 6.7 mmol), $C_4F_9CH_2CF_2CH_2CH_2OH$ (4.37 g, 13 mmol, prepared as described above), p-toluenesulfonic acid monohydrate (0.13 g, 0.67 mmol) and toluene (50 mL) were refluxed for a period of 19 h at a temperature of 113° C. The resulting pale yellow liquid (4.53 g, 90.6% yield, 72% purity) was analyzed by $^1H$ NMR and LC/MS to confirm the structure as $C_4F_9CH_2CF_2CH_2CH_2OC(O)CH_2C(=CH_2)C(O)$
$OCH_2CH_2CF_2CH_2C_4F_9$.

Compound 9

A mixture of ethanolamine (13 g, 28 mmol) and ether (30 mL) was cooled to 15° C. Perfluoro-2-methyl-3-oxahexanoyl fluoride (33 g in ether 50 mL) was added dropwise to keep the reaction temperature below 25° C. After the addition, the reaction mixture was stirred at room temperature for one hour. The solid was removed by filtration and the filtrate was washed with hydrochloric acid (0.5N, 30 mL), water (2 times 30 mL), sodium hydrogen carbonate solution (0.5N, 20 mL), water (30 mL), and sodium chloride solution (saturated, 20 mL). It was then concentrated and dried in vacuum over night at room temperature to give a white solid 35 g, yield 95%. Analysis by $^1H$ NMR and F NMR showed the product was N-(perfluoro-2-methyl-3-oxahexanoyl)-2-aminoethanol, $C_3F_7OCF(CF_3)CONHCH_2CH_2OH$.

Citraconic anhydride (0.67 g, 6.0 mmol), $C_3F_7OCF(CF_3)$
$CONHCH_2CH_2OH$ (4.44 g, 12 mmol, prepared as described above), p-toluenesulfonic acid monohydrate (0.11 g, 0.60 mmol) and toluene (50 mL) were added together and heated to reflux at 111° C., with continual stirring, for 40 h. There were two noticeable solid materials present within the toluene solution. The pinkish solid was removed and the white solid was vacuum filtered. Both materials were analyzed by LC/MS, which confirmed that the pinkish solid was the product and the white solid was unreacted alcohol (1.22 g). The product (2.98 g, 59.6% yield, 65% purity) was analyzed by $^1H$ NMR and LC/MS to confirm the structure as $C_3F_7OCF(CF_3)$
$C(O)NHCH_2CH_2OC(O)-C(CH_3)=CH_2C(O)$
$OCH_2CH_2NHC(O)CF(CF_3)OC_3F_7$.

Compound 10

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$: bp 54-57° C. at 2 mmHg (267 Pa).

Citraconic anhydride (0.75 g, 6.7 mmol), $C_4F_9CH_2CF_2CH_2CH_2OH$ (4.37 g, 13.3 mmol, prepared as described above), p-toluenesulfonic acid monohydrate (0.13 g), and toluene (50 mL) were refluxed for about 46 h at 112° C., after which only the diester was observed in the LC/MS analysis. The work-up was carried out as in example 1 to give a pale yellow liquid (2.98 g, 59.6% yield, >99% purity) which was analyzed by $^1H$ NMR and LC/MS to confirm the diester structure as $C_4F_9CH_2CF_2CH_2CH_2OC(O)C(CH_3)=CH_2C$
$(O)OCH_2CH_2CF_2CH_2C_4F_9$.

Compound 11

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$: bp 54-57° C. at 2 mmHg (267 Pa).

Trans-glutaconic acid (0.87 g, 6.7 mmol), $C_4F_9CH_2CF_2CH_2CH_2OH$ (4.37 g, 13 mmol, prepared as described above), p-toluenesulfonic acid monohydrate (0.13 g, 0.67 mmol) and toluene (50 mL) were stirred continuously together and heated to reflux at 111° C. for 24 h. The work-up procedure was carried out as in Example 1. The resulting white solid (2.52 g, 50.4% yield, 80% purity) was dried in a vacuum oven and analyzed by $^1H$ NMR and LC/MS to confirm the structure as $C_4F_9CH_2CF_2CH_2CH_2OC(O)$
$CH=CHCH_2C(O)OCH_2CH_2CF_2CH_2C_4F_9$.

Compound 12

Ethylene (56 g) was introduced to an autoclave charged with $C_4F_9(CH_2CF_2)_2I$ (714 g) and d-(+)-limonene (3.2 g), and the reactor heated at 240° C. for 12 hours. The product was isolated by vacuum distillation to provide $C_4F_9(CH_2CF_2)_2CH_2CH_2I$. A mixture of $C_4F_9(CH_2CF_2)_2CH_2CH_2I$ (10 g, 0.02 mol) and N-methylformamide (8.9 mL, 0.15 mol) was heated to 150° C. for 26 hours. The mixture was cooled to 100° C., followed by the addition of water to separate the crude ester. Ethyl alcohol (3 mL) and p-toluene sulfonic acid (0.09 g) were added and the mixture stirred at 70° C. for 0.25 hours. Ethyl formate and ethyl alcohol were removed by distillation to give a crude product. The crude product was dissolved in ether, washed with 10% by weight aqueous sodium sulfate, water and brine, in turn, and dried over magnesium sulfate. Distillation provided the product $C_4F_9(CH_2CF_2)_2CH_2CH_2OH$ (6.5 g, 83% yield): bp 94-95° C. at 2 mm Hg (266 Pa).

Trans-glutaconic acid (0.75 g, 5.8 mmol), $C_4F_9CH_2CF_2CH_2CF_2CH_2CH_2OH$ (4.54 g, 12 mmol, prepared as described above), p-toluenesulfonic acid monohydrate (0.11 g, 0.58 mmol) and toluene (50 mL) were stirred continuously together and heated to reflux at 111° C. for a period of 16 h. The progress was monitored by LC/MS and the removal of water azeotropically. The orange/yellow solid was filtered and washed with 5% sodium bicarbonate solution (50 mL). The filtrate was separated and the organic layer was washed with 5% sodium bicarbonate solution (50 mL), and then with deionized water (50 mL). The combined organic extracts were dried over anhydrous $MgSO_4$ and the toluene was then concentrated (140.30 mmHg, 67° C.). The orange solid (4.14 g, 81.5% yield, 85% purity) was dried in a vacuum oven and analyzed by $^1H$ NMR and LC/MS to confirm the structure as $C_4F_9CH_2CF_2CH_2CF_2CH_2CH_2OC(O)CH=CHCH_2C(O)O—CH_2CH_2CF_2CH_2CF_2CH_2C_4F_9$.

Compound 13

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$: bp 54-57° C. at 2 mmHg (267 Pa).

A melt reaction was undertaken by reacting maleic anhydride (2.00 g, 20 mmol) with $C_4F_9CH_2CF_2CH_2CH_2OH$ (6.69 g, 20 mmol, prepared as described above). The reaction was sustained at 70° C. for a period of 34 h, during which aliquots were taken for GC analysis. The white solid half acid/ester (8.02 g, 92.3% yield, >98% purity) was analyzed by $^1H$ NMR and LC/MS to confirm the structure as $C_4F_9CH_2CF_2CH_2CH_2OC(O)CH=CHC(O)OH$.

Compound 14

The maleate, prepared as described in Example 13, (6.68 g, 17 mmol), p-toluenesulfonic acid monohydrate (0.30 g, 1.7 mmol) and hexyl alcohol (1.60 g, 17 mmol) were mixed together along with toluene (50 mL). The mixture was stirred continuously together and heated to reflux at 114° C. for 19 h. The work-up procedure as in example 1 was conducted to produce a clear liquid (7.14 g, 89.3% yield, 98% purity), that was analyzed by $^1H$ NMR and LC/MS to confirm the structure as $C_4F_9CH_2CF_2CH_2CH_2OC(O)CH=CHC(O)O—(CH_2)_6H$.

Compound 15

The maleate, prepared as described in Example 13, (4.41 g, 10 mmol), p-toluenesulfonic acid monohydrate (0.20 g, 1.0 mmol) and $C_6F_{13}CH_2CH_2OH$ (3.77 g, 10 mmol) were added together along with toluene (50 mL). The contents were refluxed for 19 h at 114° C. and the work-up procedure was carried out as in Example 1. The pale yellow liquid (5.78 g, 72.3% yield, 90% purity) was analyzed by $^1H$ NMR and LC/MS to confirm the formation of the mixed diester and the structure as $C_4F_9CH_2CF_2CH_2CH_2OC(O)CH=CHC(O)OCH_2CH_2(CF_2)_6F$.

Example 1

The maleate, prepared as described in Compound 1, (2.62 g, 3.2 mmol) and isopropyl alcohol (IPA, 31 g) were added together at 50° C. until the mixture was dissolved; about 10 minutes. Aqueous sodium bisulfite (0.17 g, 1.6 mmol) was dissolved in deionized water (8 mL) and added dropwise to the isopropyl alcohol solution, which was then heated to reflux (86° C.) for 26 h. The isopropyl alcohol and water were removed by rotary evaporation followed by drying in a vacuum oven at 50° C. to generate a viscous yellow liquid (1.70 g, 57.6% yield, 75% purity), which was confirmed to be the diester sulfonate by $^1H$ NMR and LC/MS analyses to confirm the structure as $C_3F_7OCF(CF_3)C(O)NHCH_2CH_2OC(O)CH_2CH(SO_3Na)C(O)O—CH_2CH_2NHC(O)CF(CF_3)OC_3F_7$.

The product was evaluated for CMC and surface tension beyond the CMC by Test Method 1; the results are shown in Table 2.

Example 2

The maleate, prepared as described in Compound 2, (7.74 g, 11 mmol) and isopropyl alcohol (31 g) were stirred continuously together. The temperature was raised to 61° C. and then a solution of sodium bisulfite (1.09 g, 11 mmol), dissolved in deionized water (53 mL), was added dropwise. The mixture was heated to reflux at an elevated temperature of 82° C. for 24 h. The solution was concentrated to remove the isopropyl alcohol/water solution. The remaining pale yellow liquid was dried overnight in an oven to produce a white solid (6.96 g, 78.8% yield, 98% purity) and was then analyzed by $^1H$ NMR and LC/MS to confirm the structure as $C_4F_9CH_2CF_2CH_2CH_2OC(O)—CH_2CH(SO_3Na)C(O)O—CH_2CH_2CF_2CH_2C_4F_9$. The product was evaluated for CMC and surface tension beyond the CMC by Test Method 1, with results shown in Table 2, and spreading on cyclohexane by Test Method 2, with results shown in Table 3.

Example 3

The maleate, prepared as described in Compound 3, (2.88 g, 3.3 mmol) and isopropyl alcohol (31 g) were stirred continuously at 82° C., with the addition of aqueous sodium bisulfite (1.54 g, 15 mmol), dissolved in deionised water (20 mL), for 28 h. The white solid (2.58 g, 80.1% yield, >95% purity) was collected by concentrating the isopropyl alcohol/water solution and then dried in a vacuum oven overnight. The product was analyzed by $^1H$ NMR and LC/MS to confirm the structure as $C_4F_9CH_2CF_2CH_2CF_2CH_2CH_2OC(O)CH_2CH(SO_3Na)C(O)O—CH_2CH_2CF_2CH_2CF_2CH_2C_4F_9$. The product was evaluated for CMC and surface tension beyond the CMC by Test Method 1, with results shown in Table 2, and spreading on cyclohexane by Test Method 2, with results shown in Table 3.

Example 4

The maleate, prepared as described in Compound 4, (4.10 g, 5.5 mmol), isopropyl alcohol (31 g) and aqueous sodium bisulfite (0.28 g, 2.8 mmol) dissolved in deionized water (14 mL) were stirred continuously for 18 h at a temperature of 82° C. The white solid (3.36 g, 71.9% yield, >95% purity) was collected by rotary evaporating the isopropyl alcohol/water solution and then the product was dried in a vacuum oven. The product was analyzed by $^1H$ NMR and LC/MS to confirm conversion to the diester sulfonate and the structure as $C_3F_7OCF_2CF_2CH_2CH_2OC(O)CH_2CH(SO_3Na)C(O)O—CH_2CH_2CF_2CF_2OC_3F_7$. The product was evaluated for CMC and surface tension beyond the CMC by Test Method 1, with results shown in Table 2, and spreading on cyclohexane by Test Method 2, with results shown in Table 3.

Example 5

The maleate, prepared as described in Compound 5, (1.49 g, 1.8 mmol), isopropyl alcohol (31 g) and aqueous sodium bisulfite (0.29 g, 2.8 mmol) dissolved in deionised water (14 mL) were mixed together and refluxed for 27 h at 82° C. The isopropyl alcohol was concentrated and the white solid (1.46 g, 87.1% yield, >97% purity) obtained was dried in a vacuum oven and analyzed by $^1$H NMR and LC/MS to confirm the structure as $C_3F_7OCFHCF_2OCH_2CH_2OCH_2CH_2OC(O)CH_2CH(SO_3Na)C(O)O—CH_2CH_2OCH_2CH_2OCF_2CFHOC_3F_7$. The product was evaluated for CMC and surface tension beyond the CMC by Test Method 1, with results shown in Table 2, and spreading on cyclohexane by Test Method 2, with results shown in Table 3.

Example 6

The maleate, prepared as described in Compound 6, (7.54 g, 8.7 mmol) and isopropyl alcohol (31 g) were heated to 50° C. until the solid had dissolved in solution. A solution of aqueous sodium bisulfite (0.91 g, 8.7 mmol) dissolved in deionized water (43 mL) was transferred to the mixture and the contents were refluxed at 82° C. for 20 h. The isopropyl alcohol/water solution was removed by rotary evaporation to attain the orange/brown solid (7.22 g, 87.3% yield, 92% purity). The product was analyzed by $^1$H NMR and LC/MS to confirm the structure as $C_2F_5CH_2CH_2[(CF_2CF_2)(CH_2CH_2)]_k OC(O)CH_2CH(SO_3Na)C(O)O—[(CH_2CH_2)(CF_2CF_2)]_k CH_2CH_2C_2F_5$, wherein k is a mixture of 2 and 3 in a 2:1 ratio. The product was evaluated for CMC and surface tension beyond the CMC by Test Method 1; the results are shown in Table 2.

Example 7

The itaconate, prepared as described in Compound 7, (3.60 g, 4.3 mmol) and isopropyl alcohol (31 g) were stirred continuously together. An aqueous solution of sodium bisulfite (0.45 g, 4.3 mmol) dissolved in deionized water (21 mL) was added slowly to the solution and the temperature was raised to 82° C. for 23 h. The isopropyl alcohol/water was concentrated to leave the yellow gel-like product (3.73 g, 92.1% yield, 75% purity), which was placed in a vacuum oven overnight analyzed by $^1$H NMR and LC/MS to confirm the structure as $C_3F_7OCF(CF_3)C(O)NHCH_2CH_2OC(O)C_3H_5(SO_3Na)C(O)O—CH_2CH_2NHC(O)CF(CF_3)OC_3F_7$. The product was evaluated for CMC and surface tension beyond the CMC by Test Method 1, with results shown in Table 2, and spreading on cyclohexane by Test Method 2, with results shown in Table 3.

Example 8

The itaconate, prepared as described in Compound 8, (2.00 g, 2.7 mmol), isopropyl alcohol (31 g) and aqueous sodium bisulfite (0.28 g, 2.7 mmol) dissolved in deionized water (14 mL) were refluxed for 22 h at 82° C. The white solid (precipitate) was filtered off and washed with deionized water (50 mL) to remove unreacted $NaHSO_3$. The white dry solid (2.11 g, 91.5% yield, >95% purity) was analyzed by $^1$H NMR and LC/MS to confirm the structure as $C_4F_9CH_2CF_2CH_2CH_2OC(O)C_3H_5(SO_3Na)C(O)OCH_2CH_2CF_2CH_2C_4F_9$. The product was evaluated for CMC and surface tension beyond the CMC by Test Method 1, with results shown in Table 2, and spreading on cyclohexane by Test Method 2, with results shown in Table 3.

Example 9

The citraconate, prepared as described in Compound 9, (2.96 g, 3.5 mmol), and isopropyl alcohol (31 g) were stirred continuously together and heated to reflux. A solution of aqueous sodium bisulfite (0.37 g, 3.5 mmol) dissolved in deionized water (18 mL) was added dropwise to the mixture. The solution was maintained at 82° C. for 23 h. The solution was concentrated and two noticeable layers were observed. The small top layer was yellow in colour and the bottom was white. Each layer was analyzed by $^1$HNMR, which confirmed that the top layer was likely to be impurities. The product was tested in isopropyl alcohol and also in water, and the alcohol was also similarly tested. The results indicated that the product was soluble in water but insoluble in isopropyl alcohol, and the opposite was true for the alcohol. Therefore, if the impurity layer contained some alcohol this would be removed by filtration when water was added. If any of the starting acid remained this would not affect the surface tension results. The bottom layer (2.62 g, 78.8% yield, 85% purity) was analyzed by $^1$H NMR and LC/MS to confirm the structure as $C_3F_7OCF(CF_3)C(O)NHCH_2CH_2OC(O)C_3H_5(SO_3Na)C(O)O—CH_2CH_2NHC(O)CF(CF_3)OC_3F_7$.

The product was evaluated for CMC and surface tension beyond the CMC by Test Method 1; the results are shown in Table 2.

Example 10

The citraconate, prepared as described in Compound 10, (2.70 g, 3.6 mmol) and isopropyl alcohol (31 g) were mixed together at 50° C. until dissolved; about 10 minutes. Aqueous sodium bisulfite (1.54 g, 14.8 mmol) was dissolved in deionized water (15 mL) and added dropwise to the isopropyl alcohol solution, which was then heated to about 82° C. for about 22 h. The isopropyl alcohol and water were removed by rotary evaporation followed by drying in a vacuum oven at 50° C. to give an off-white solid (1.56 g, 50.8% yield, Purity: >99%), which was analyzed by $^1$H NMR and LC/MS to confirm the formation of the diester sulfonate and the structure as $C_4F_9CH_2CF_2CH_2CH_2OC(O)C_3H_5(SO_3Na)—C(O)OCH_2CH_2CF_2CH_2C_4F_9$. The product was evaluated for CMC and surface tension beyond the CMC by Test Method 1, with results shown in Table 2, and spreading on cyclohexane by Test Method 2, with results shown in Table 3.

Example 11

The trans-glutaconate, prepared as described in Compound 11, (2.52 g, 3.4 mmol) was added to isopropyl alcohol (31 g) and heated to 60° C. At this point a solution of sodium bisulfite (0.31 g, 3.0 mmol) dissolved in deionized water (15 mL) was added dropwise, and the temperature was raised to 82° C. for 22 h. The pale yellow solid (2.26 g, 78.8% yield, 80% purity) was analyzed by $^1$H NMR and LC/MS to confirm the structure as $C_4F_9CH_2CF_2CH_2CH_2OC(O)C_3H_5(SO_3Na)C(O)OCH_2CH_2CF_2CH_2—C_4F_9$. The product was evaluated for CMC and surface tension beyond the CMC by Test Method 1; the results are shown in Table 2.

Example 12

The trans-glutaconate, prepared as described in Compound 12, (4.08 g, 4.6 mmol) was added to isopropyl alcohol (31 g) and heated to 50° C. A solution of sodium bisulfite (0.31 g, 3.0 mmol) dissolved in deionized water (15 mL) was added dropwise to the solution and the mixture was heated to 82° C. for 23 h. The yellow solid (3.94 g, 86.3% yield, 90% purity) was collected by rotary evaporating the isopropyl alcohol/water solution and analyzed by $^1$H NMR and LC/MS to confirm the structure as $C_4F_9CH_2CF_2CH_2CF_2CH_2CH_2OC(O)C_3H_5$ $(SO_3Na)C(O)O$—$CH_2CH_2CF_2CH_2CF_2CH_2C_4F_9$.

The product was evaluated for CMC and surface tension beyond the CMC by Test Method 1; the results are shown in Table 2.

Example 13

The maleate, prepared as described in Compound 13, (4.20 g, 9.4 mmol) and isopropyl alcohol (31 g) were heated to approximately 50° C. to allow for the solid to dissolve in solution. Aqueous sodium bisulfite (0.99 g, 9.4 mmol) dissolved in deionized water (47 mL) was transferred to the solution and the contents were refluxed for 22 h at 82° C. The isopropyl alcohol/water solution was rotary evaporated to leave the white solid (4.14 g, 82.8% yield, 90% purity) that was analyzed by $^1$H NMR and LC/MS to confirm the structure as $C_4F_9CH_2CF_2CH_2CH_2OC(O)CH_2CH(SO_3Na)C(O)OH$. The product was evaluated for CMC and surface tension beyond the CMC by Test Method 1; the results are shown in Table 2.

Example 14

The mixed diester, prepared as described in Compound 14, (7.10 g, 13.9 mmol) and isopropyl alcohol (32 g) were stirred continuously together and heated to 50° C. until the two liquids became miscible. Aqueous sodium bisulfite (1.45 g, 13.9 mmol) dissolved in deionized water (70 mL) was transferred to the mixture and the contents were refluxed for 22 h at 82° C. The isopropyl alcohol/water solution was evaporated off and the white gel product (6.26 g, 73.3% yield, 98% purity) was dried in vacuum oven for 2 h. The product was analyzed by $^1$H NMR and LC/MS to confirm the structure as $C_4F_9CH_2CF_2CH_2CH_2OC(O)CH_2CH(SO_3Na)C(O)O(CH_2)_6H$. The product was evaluated for CMC and surface tension beyond the CMC by Test Method 1, with results shown in Table 2, and spreading on cyclohexane by Test Method 2, with results shown in Table 3.

Example 15

The mixed diester, prepared as in Compound 15 (5.78 g, 7.5 mmol) and isopropyl alcohol (31 g) were added together and heated to 60° C. for 10 minutes. A solution of sodium bisulfite (0.78 g, 7.5 mmol) dissolved in deionized water (37 mL) was added to the solution and the mixture was heated to reflux at 82° C. for a period of 20 h. The isopropyl alcohol/water solution was rotary evaporated off to leave a colorless gel product (4.26 g, 65% yield, 98% purity) that was analyzed by $^1$H NMR and LC/MS to confirm the structure as $C_4F_9CH_2CF_2CH_2CH_2OC(O)CH_2CH(SO_3Na)C(O)OCH_2CH_2(CF_2)_6F$. The product was evaluated for CMC and surface tension beyond the CMC by Test Method 1; the results are shown in Table 2.

Comparative Example A

Maleic anhydride (0.63 g, 6.5 mmol), 1H,1H,2H,2H-perfluoro-1-octanol (4.74 g, 13 mmol), p-toluenesulfonic acid monohydrate (p-TsOH) (0.19 g, 1.0 mmol) and toluene (50 mL) were added to a flask and heated to reflux for 96 hours at 111° C. The solution was separated and extracted with two washings of 5% sodium bicarbonate (50 mL each). The combined organic extracts were dried over anhydrous magnesium sulfate, and concentrated to remove the toluene at 140.30 mmHg (18.7 kPa) and 67° C.). The structure of the resulting liquid product di(1H,1H,2H,2H-perfluorooctyl)maleate (4.88 g, 93.4% yield, >80% purity) was confirmed by $^1$H NMR and LC/MS.

Di(1H,1H,2H,2H-perfluorooctyl)maleate (4.70 g, 5.8 mmol, prepared as described above) was added to isopropyl alcohol (isopropyl alcohol, 31 g) and heated to 50° C. for a period of 10 min. with continual stirring. A solution of sodium bisulfite (0.61 g, 5.8 mmol) dissolved in deionized water (10 mL) was added dropwise to the solution. The mixture was refluxed for 22 h at 82° C. The progress was checked by LC/MS and a further addition of aqueous sodium bisulfite (0.61 g, 5.9 mmol) was added. The mixture was refluxed for a further 70.3 h. The isopropyl alcohol/water solution was removed by rotary evaporation to produce a white solid. (2.70 g, 52.2% yield, 99% purity). The product composition was confirmed by $^1$H NMR and LC/MS as the sodium salt of di(1H,1H,2H,2H-perfluorooctyl)maleate-2-sulfosuccinate. The product was evaluated for CMC and surface tension beyond the CMC by Test Method 1; the results are shown in Table 1.

Comparative Example B 1H,1H,2H,2H-perfluorooctanol (8.02 g, 22 mmol), dicyclohexylcarbodiimide (DCC) (4.27 g, 21 mmol) and dichloromethane $CH_2Cl_2$, 35 mL) were added to a flask, equipped with a nitrogen inlet, overhead stirrer and two stoppers. The solution was cooled to 0° C. and the citraconic acid (1.28 g, 9.8 mmol) dissolved in tetrahydrofuran (15 mL) was added dropwise. The solution was stirred for 10 min. and then the ice bath was removed to allow the solution to warm to room temperature. The mixture was left to stir overnight. The resulting mixture was filtered to remove the traces of 1,3-dicylcohexylurea that was produced as a by-product and then washed with excess tetrahydrofuran (50 mL). The tetrahydrofuran and $CH_2Cl_2$ were concentrated at 378.14 mmHg (kPa) and 46° C.) and the product was dried in a vacuum oven for 3 hours. The product was analyzed through $^1$H NMR and LC/MS, which indicated the conversion to monoester. A similar procedure was carried out again but with the addition of another mole of alcohol. The alcohol (6.30 g, 13 mmol), DCC (2.63 g, 13 mmol) and $CH_2Cl_2$ (35 mL) were added to the flask and cooled to 0° C. The monoester, that was produced previously, was re-dissolved in tetrahydrofuran (15 mL) and added dropwise to the solution. The work-up method was carried out and the resulting product was a pale yellow liquid (6.46 g, 80.0% yield, 75% purity). The product was analyzed by $^1$H NMR and LC/MS to confirm the structure as di(1H,1H,2H,2H-perfluorooctyl)citraconate.

Di(1H,1H,2H,2H-perfluorooctyl)citraconate (4.99 g, 6.1 mmol, prepared as described above) and isopropyl alcohol (32 g) were transferred to a flask and heated to 50° C. for 10 min. A solution of aqueous sodium bisulfite (1.53 g, 15 mmol) dissolved in deionized water was added to the solution and heated to reflux (82° C.) for 22 h. The white solid was dried in an oven overnight (2.98 g, 53.0% yield, 95% purity). The product composition was confirmed by $^1$H NMR and LC/MS as the sodium salt of di(1H,1H,2H,2H-perfluorooctyl) citraconate-2-sulfosuccinate. The product was evaluated for CMC and surface tension beyond the CMC by Test Method 1, with results shown in Table 2, and spreading on cyclohexane by Test Method 2, with results shown in Table 3.

Comparative Example C

Maleic anhydride (17.2 g, 176 mmol), 1H,1H,2H,2H,-perfluorohexanol (93.1 g, 353 mmol), p-toluenesulfonyl hydroxide (p-TsOH) (3.4 g, 17.6 mmol) and toluene (500 mL) were heated to reflux for 8 h. An additional amount of p-TsOH (3.4 g, 17.6 mmol) was added after 4 h of reflux. The solution was stirred overnight at room temperature. The solution was diluted with ethyl acetate (500 mL) and washed three times with brine (250 mL each). The combined extracts were washed with a further washing of ethyl acetate (300 mL). The combined organics were dried over anhydrous $MgSO_4$ and concentrated to yield a colorless oil (85.8 g, 80% yield, 98% purity). The structure of the product was confirmed by $^1H$ NMR and LC/MS as di(1H,1H,2H,2H-perfluorohexyl) maleate.

Di(1H,1H,2H,2H-perfluorohexyl)maleate (1.5 g, 2.5 mmol, prepared as described above) was added to isopropyl alcohol (32 g) and heated for a period of 10 min. until the two liquids became miscible. A solution of sodium bisulfite (1.5 g, 14 mmol) dissolved in deionized water (15 mL) was transferred to the flask and the contents were heated to reflux at 82° C. for 22 h. The white solid product resulted after the removal of isopropyl alcohol/water solution (0.98 g, 55.8% yield, 99% purity). The product composition was confirmed by $^1H$ NMR and LC/MS as the sodium salt of di(1H,1H,2H,2H-perfluorohexyl)) maleate-2-sulfosuccinate. The product was evaluated for CMC and surface tension beyond the CMC by Test Method 1, with results shown in Table 2, and spreading on cyclohexane by Test Method 2, with results shown in Table 3.

Comparative Example D

Ethylene (25 g) was introduced to an autoclave charged with $C_4F_9CH_2CF_2I$ (217 g) and d-(+)-limonene (1 g), and the reactor heated at 240° C. for 12 hours. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 hours. The reaction was quenched with ice-cold 1.5 wt % $Na_2SO_3$ aqueous solution and heated at 95° C. for 0.5 hours. The bottom layer was separated and washed with 10 wt % aqueous sodium acetate and distilled to provide $C_4F_9CH_2CF_2CH_2CH_2OH$: bp 54-57° C. at 2 mmHg (267 Pa).

Trans-β-hydromuconic acid (0.94 g, 6.5 mmol), p-toluenesulfonic acid monohydrate (0.12 g, 0.65 mmol), $C_4F_9CH_2CF_2CH_2CH_2OH$ (4.29 g, 13 mmol) and toluene were added together and the contents were heated to reflux at 111° C. for 25 h. The work-up as in example 1 was conducted. The white solid (3.82 g, 76.4% yield, 95% purity) analyzed by $^1H$ NMR and LC/MS to confirm the structure as $C_4F_9CH_2CF_2CH_2CH_2OC(O)CH_2CH=CHCH_2C(O)$ $OCH_2CH_2CF_2CH_2$—$C_4F_9$.

The trans-β-hydromuconate, prepared as described above, (3.80 g, 5.0 mmol) was added to isopropyl alcohol (31 g) and heated to 60° C. A solution of aqueous sodium bisulfite (0.52 g, 5.0 mmol) was dissolved in deionized water and transferred to the mixture. The temperature was raised to 82° C. and maintained for 22 h. The white precipitate was collected by vacuum filtration and the filtrate was concentrated to remove the isopropyl alcohol/water solution. The white solid (3.88 g, 89.9% yield, 98% purity was analyzed by $^1H$ NMR and LC/MS to confirm the structure as $C_4F_9CH_2CF_2CH_2CH_2OC$ $(O)CH_2CH(SO_3Na)CH_2CH_2C(O)O$— $CH_2CH_2CF_2CH_2C_4F_9$. The product was evaluated for CMC and surface tension beyond the CMC by Test Method 1; the results are shown in Table 2.

Comparative Example E $C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing Then the product was collected in a bottle. The product was distilled giving 80 g of $C_3F_7OCF_2CF_2CH_2CH_2I$ in 80% yield. The boiling point was 56-60° C. at 25 mm Hg (3.3 kPa).

A mixture of $C_3F_7OCF_2CF_2CH_2CH_2I$ (300 g, 0.68 mol, prepared as described above) and N-methyl-formamide (300 mL), was heated to 150° C. for 26 h. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to give 199 g of $C_3F_7OCF_2CF_2CH_2CH_2OH$ in 85% yield. The boiling point was 71-73° C. at 40 mm Hg (5.3 kPa).

Trans-β-hydromuconic acid (0.94 g, 6.5 mmol), $C_3F_7OCF_2CF_2CH_2CH_2OH$ (4.30 g, 13 mmol, prepared as described above), p-toluenesulfonic acid monohydrate H (0.13 g, 0.65 mmol) and toluene (50 mL) were stirred continuously together and heated to reflux (111° C. for 25 h). The work-up was carried out to produce a pale yellow liquid (3.90 g, 78.0% yield, 99% purity), which was analyzed by $^1H$ NMR and LC/MS to confirm the structure as $C_3F_7OCF_2CF_2CH_2CH_2OC(O)CH_2CH=CHCH_2C(O)O$— $CH_2CH_2CF_2CF_2OC_3F_7$.

The trans-β-hydromuconate, prepared as described above, (3.88 g, 5.1 mmol) was stirred continuously with isopropyl alcohol (31 g) for a period of 10 mins at an elevated temperature of 65° C. A solution of sodium bisulfite (0.29 g, 2.8 mmol) dissolved in deionized water (14 mL) was added dropwise to the mixture. The temperature was raised to 82° C. and maintained for a period of 22 h. The solution was concentrated to remove the isopropyl alcohol, and the resulting liquid was left in a vacuum oven overnight. The white solid (3.72 g, 84.4% yield, 87% purity) obtained was analyzed by $^1H$ NMR and LC/MS to confirm the structure as $C_3F_7OCF_2CF_2CH_2CH_2OC(O)CH_2CH(SO_3Na)CH_2CH_2C$ $(O)O$—$CH_2CH_2CF_2CF_2OC_3F_7$. The product was evaluated for CMC and surface tension beyond the CMC by Test Method 1; the results are shown in Table 2.

TABLE 1

Comparative Examples and Surface Tension Measurements

| Comparative Example | $R_f$ | X | CMC (wt %) | Surface Tension beyond CMC (mN/m) |
|---|---|---|---|---|
| Comp. Ex. A | $C_6F_{13}$ | —$CH_2$—CH—($SO_3M$)— | 0.024 | 13.8 |
| Comp. Ex. B | $C_6F_{13}$ | —$CH_2$—CH($CH_2$—$SO_3M$)— | 0.068 | 16.3 |
| Comp. Ex. C | $C_4F_9$ | —$CH_2CH$—($SO_3M$)— | 0.26 | 17.1 |

TABLE 1-continued

Comparative Examples and Surface Tension Measurements

| Comparative Example | $R_f$ | X | CMC (wt %) | Surface Tension beyond CMC (mN/m) |
|---|---|---|---|---|
| Comp. Ex. D | $C_4F_9CH_2CF_2CH_2$—$CH_2$— | —$CH_2CH(SO_3M)$—$CH_2CH_2$— | 0.33 | 18.0 |
| Comp. Ex. E | $C_3F_7OCF_2CF_2CH_2$—$CH_2$— | —$CH_2CH(SO_3M)$—$CH_2CH_2$— | 0.88 | 20.8 |

TABLE 2

Formulae 1A, 1B, and 1C and Surface Tension Measurements

| Ex. | $R_a$ | X | Critical Micelle Concn. (wt %) | Surface Tension Beyond CMC (mN/m) |
|---|---|---|---|---|
| 1 | $C_3F_7OCF(CF_3)CONH$—$CH_2CH_2$— | —$CH_2CH(SO_3M)$— | 0.016 | 22.0 |
| 2 | $C_4F_9CH_2CF_2CH_2$— | —$CH_2CH(SO_3M)$— | 0.051 | 18.9 |
| 3 | $C_4F_9CH_2CF_2CH_2CF_2$—$CH_2CH_2$— | —$CH_2CH(SO_3M)$— | 0.014 | 20.7 |
| 4 | $C_3F_7OCF_2CF_2CH_2CH_2$— | —$CH_2CH(SO_3M)$— | 0.034 | 17.1 |
| 5 | $C_3F_7OCFHCF_2O$—$CH_2CH_2OCH_2CH_2$— | —$CH_2CH(SO_3M)$— | 0.039 | 17.8 |
| 6 | $C_2H_5CH_2CH_2[(CF_2CF_2)_i$—$(CH_2CH_2)_j]_k$ | —$CH_2CH(SO_3M)$— | 0.028 | 21.1 |
| 7 | $C_3F_7OCF(CF_3)CONH$—$CH_2CH_2$— | —$CH_2CH(CH_2SO_3M)$— | 0.083 | 18.2 |
| 8 | $C_4F_9CH_2CF_2CH_2$— | —$CH_2CH(CH_2SO_3M)$— | 0.0095 | 19.4 |
| 9 | $C_3F_7OCF(CF_3)CONH$—$CH_2CH_2$— | —$CH(CH_3)CH(SO_3M)$— | 0.095 | 25.6 |
| 10 | $C_4F_9CH_2CF_2CH_2$— | —$CH(CH_3)CH(SO_3M)$— | 0.019 | 16.8 |
| 11 | $C_4F_9CH_2CF_2CH_2$— | —$CH_2CH(SO_3M)CH_2$— | 0.042 | 18.0 |
| 12 | $C_4F_9CH_2CF_2CH_2CF_2$—$CH_2CH_2$— | —$CH_2CH(SO_3M)CH_2$— | 0.030 | 18.2 |
| | $R_a/R$ | | | |
| 13* | $C_4F_9CH_2CF_2CH_2CH2$—/—H | —$CH_2CH(SO_3M)$— | 0.064 | 19.7 |
| 14 | $C_4F_9CH_2CF_2CH_2CH_2$—/—$(CH_2)_6H$ | —$CH_2CH(SO_3M)$— | 0.038 | 16.0 |
| | $R_a/R_f$ | | | |
| 15 | $C_4F_9CH_2CF_2CH_2CH_2$—/—$(CF_2)_6F$ | —$CH_2CH(SO_3M)$— | 0.023 | 20.8 |

*Example 13 was measured at pH 3.0. Since the $R_a$ is H, the performance of the compound is sensitive to pH.

Table 2 shows that the surfactants of the invention gave low critical micelle concentrations (less than 0.1 weight percent) and low surface tension levels beyond CMC (less than 20 mN/m in water). Table 1 provides data for Comparative Examples. Comparative Example C, having an $R_f$ of $C_4F_9$ contained a similar fluorine level to the Examples of the invention, but had a far higher CMC value, thus indicating superior performance by the Examples of the invention. Comparative Examples A and B each contained an $R_f$ of $C_6F_{13}$, which was a higher fluorine level than the Examples of the invention. The Examples of the invention had CMC values similar to Comparative Examples A and B despite the lower level of fluorine. Thus the Examples of the invention had a higher level of fluorine efficiency in providing comparable performance with less fluorine present. Beyond the CMC all of the examples demonstrated comparable surface tension.

TABLE 3

Spreading on Cyclohexane

| Ex. # | Hydrocarbon surfactant Trials (I) and (II) | Spreading on cyclohexane (extent and time) | Performance Category |
|---|---|---|---|
| 2 | I) SIMULSOL SL8 | 30% in 30 s | Good |
| | II) TRITON X100 | Floats without spreading | Fair |
| 3 | I) SIMULSOL SL8 | 50% in 30 s | Good |
| | II) TRITON X100 | 100% in 30 seconds | Excellent |
| 4 | I) SIMULSOL SL8 | Sink immediately | Poor |
| | II) TRITON X100 | 70% in 40 s | Good |
| 5 | I) SIMULSOL SL8 | 100% in 6 seconds | Excellent |
| | II) TRITON X100 | 50% in 30 s | Good |
| 7 | I) SIMULSOL SL8 | 50% in 10 s | Good |
| | II) TRITON X100 | Floats without spreading | Fair |
| 8 | I) SIMULSOL SL8 | 20% in 20 s | Good |
| | II) TRITON X100 | 100% in 25 s | Excellent |
| 10 | I) SIMULSOL SL8 | 10% in 20 s | Good |
| | II) TRITON X100 | Sink immediately | Poor |
| 14 | I) SIMULSOL SL8 | 100% in 3 s | Excellent |
| | II) TRITON X100 | 100% in 3 s | Excellent |
| B | I) SIMULSOL SL8 | Sink immediately | Poor |
| | II) TRITON X100 | Sink immediately | Poor |
| C | I) SIMULSOL SL8 | Sink immediately | Poor |
| | II) TRITON X100 | Sink immediately | Poor |

Table 3 shows that the surfactants of the present invention, when combined with hydrocarbon surfactant SIMULSOL SL8 or TRITON X100 in an aqueous formulation, spread more quickly and more completely across cyclohexane than either Comparative Example B or C, which both sank. Spreading across cyclohexane is predictive of an effective fire fighting foam. Table 3 shows that low critical micelle concentrations and low Surface Tension levels beyond CMC are necessary but not sufficient criteria for an effective fire fighting foam.

What is claimed is:

1. A compound of Formula 1A, 1B, or 1C $$(R_a-O-CO-)_2X \quad \text{Formula 1A}$$

$$R_a-O-CO-X-CO-O-(CH_2CH_2)R_f \quad \text{Formula 1B}$$

$$R_a-O-CO-X-CO-O-R \quad \text{Formula 1C}$$

wherein
$R_a$ is the group
(i) $R_f(CH_2CF_2)_d-(C_gH_{2g})-$;
(ii) $R_fOCF_2CF_2-(C_gH_{2g})-$;
(iii) $R_fOCFHCF_2-O-(CH_2CH_2O)_v-(C_gH_{2g})-$;
(iv) $R_fOCFHCF_2O(C_wH_{2w})$;
(v) $R_fOCF(CF_3)CONH-(C_gH_{2g})-$; or
(vi) $R_f(CH_2)_h[(CF_2CF_2)_i(CH_2CH_2)_j]_k$
each $R_f$ is independently $C_cF_{(2c+1)}$;
c is 2 to about 6;
d is 1 to about 3;
g is 1 to 4;
v is 1 to about 4;
w is from about 3 to about 12;
h is 1 to about 6;
i, j, and k are each independently 1, 2, or 3, or a mixture thereof;
provided that the total number of carbon atoms in group (vi) is from about 8 to about 22;
X is a linear or branched difunctional alkyl sulfonate group $$-C_eH_{(2e-1)}(SO_3M)-,$$

wherein e is 2 or 3;
M is a monovalent cation selected from the group consisting of hydrogen, ammonium, and alkali metal;
R is H or a linear or branched alkyl group $C_bH_{(2b+1)}-$; and
b is from 1 to about 18.

2. The compound of claim 1 wherein $R_a$ is $R_f(CH_2CF_2)_d-(C_gH_{2g})-$; $R_fOCF_2CF_2-(C_gH_{2g})-$; $R_f$ $OCFHCF_2O(CH_2CH_2O)_v-(C_gH_{2g})-$; or $R_fOCFHCF_2O(C_wH_{2w})-$.

3. The compound of claim 1 wherein c is 3 or 4 or 6.

4. The compound of claim 1 wherein X is $CH_2CH(SO_3M)$, $CH_2CH(CH_2SO_3M)$, $CH(CH_3)CH(SO_3M)$, $CH_2CH(SO_3M)CH_2$, or $CH_2CH(SO_3M)CH_2CH_2$.

5. The compound of claim 2 wherein d is 1, g is 2, and $R_f$ is $C_3F_7$ or $C_4F_9$.

6. The compound of claim 5 wherein X is $C_3H_5(SO_3Na)$ or $CH_2CH(SO_3Na)$.

7. The compound of claim 1 wherein $R_a$ is $C_4F_9CH_2CF_2CH_2CH_2$ or $C_3F_7CH_2CF_2CH_2CH_2$.

8. A method of altering the surface behavior of a liquid comprising adding to the liquid a compound of claim 1 or a mixture thereof.

9. The method of claim 8 wherein the altering of surface behavior is lowering the surface tension.

10. The method of claim 8 wherein the surface behavior is selected from the group consisting of wetting, penetration, spreading, leveling, flowing, emulsifying, dispersing, repelling, releasing, lubricating, etching, bonding, and stabilizing.

11. The method of claim 8 wherein the liquid is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent.

* * * * *